United States Patent
Mo et al.

(10) Patent No.: US 11,440,965 B2
(45) Date of Patent: Sep. 13, 2022

(54) ANTI-OX40 ANTIBODY

(71) Applicant: NANJING UMAB-BIOPHARMA CO., LTD., Nanjing (CN)

(72) Inventors: Shifu Mo, Nanjing (CN); Xun Yin, Nanjing (CN); Jing Zhao, Nanjing (CN)

(73) Assignee: NANJING UMAB-BIOPHARMA CO., LTD., Nanjing (CN)

( * ) Notice: Subject to any disclaimer, the term of this patent is extended or adjusted under 35 U.S.C. 154(b) by 0 days.

(21) Appl. No.: 16/958,557

(22) PCT Filed: Dec. 12, 2018

(86) PCT No.: PCT/CN2018/120520
§ 371 (c)(1),
(2) Date: Jun. 26, 2020

(87) PCT Pub. No.: WO2019/128708
PCT Pub. Date: Jul. 4, 2019

(65) Prior Publication Data
US 2021/0269539 A1    Sep. 2, 2021

(30) Foreign Application Priority Data

Dec. 29, 2017  (CN) .......................... 201711476160.3

(51) Int. Cl.
*C07K 16/28*      (2006.01)
*A61K 39/395*     (2006.01)
*G01N 33/68*      (2006.01)
*A61K 39/00*      (2006.01)

(52) U.S. Cl.
CPC .......... *C07K 16/2878* (2013.01); *G01N 33/68* (2013.01); *A61K 2039/505* (2013.01); *C07K 2317/24* (2013.01); *C07K 2317/565* (2013.01); *C07K 2317/732* (2013.01); *C07K 2317/74* (2013.01); *C07K 2317/76* (2013.01); *G01N 2333/70578* (2013.01)

(58) Field of Classification Search
None
See application file for complete search history.

(56) References Cited

FOREIGN PATENT DOCUMENTS

| CN | 103717263 A | 4/2014 |
|---|---|---|
| CN | 106103486 A | 11/2016 |
| CN | 107074953 A | 8/2017 |
| CN | 107106665 A | 8/2017 |
| CN | 108218990 A | 6/2018 |
| TW | 201734046 A | 10/2017 |
| WO | 2015/095423 A2 | 6/2015 |
| WO | 2016/081384 A1 | 5/2016 |
| WO | 2016/179517 A1 | 11/2016 |
| WO | 2017/050729 A1 | 3/2017 |

OTHER PUBLICATIONS

Extended European Search Report dated Nov. 30, 2021, issued in related EP Application No. 18893920.1, filed Dec. 12, 2018, 10 pages.
Takaori-Kondo, et al., "Both Amino- and Carboxyl-Terminal Domains of TRAF3 Negatively Regulate NF- κB Activation Induced by OX40 Signaling," Biochemical and Biophysical Research Communications 272(3):856-863, Jun. 2020.
Hou, X.-J., et al., "The Preparation and Preliminary Identification of Human Anti-OX40 Monoclonal Antibody," Letters in Biotechnology 28(3):242-248, Feb. 2006.
Search Report dated Mar. 4, 2020, issued in CN Application No. 201711476160.3, filed Dec. 29, 2017, 3 pages.
International Search Report dated Mar. 13, 2019, issued in International Application No. PCT/CN2018/120520, filed Dec. 12, 2018, 9 pages.
Written Opinion dated Mar. 13, 2019, issued in International Application No. PCT/CN2018/120520, filed Dec. 12, 2018, 8 pages.
International Preliminary Report on Patentability dated Jun. 30, 2020, issued in International Application Mo. PCT/CN2018/120520, filed Dec. 12, 2018, 10 pages.

*Primary Examiner* — Phillip Gambel
(74) *Attorney, Agent, or Firm* — Christensen O'Connor Johnson Kindness PLLC

(57) ABSTRACT

Provided is an isolated antibody or antigen binding fragment thereof. The isolated antibody or antigen binding fragment thereof can be used to prepare a medicament for treating tumors.

34 Claims, 10 Drawing Sheets

Specification includes a Sequence Listing.

ANTI-OX40 ANTIBODY

CROSS-REFERENCE TO RELATED APPLICATIONS

This application is a National Stage of International Application No. PCT/CN2018/120520, filed Dec. 12, 2018, which claims the priority of the Chinese invention patent application No. 2017114761603, entitled "Isolated Antibody or Antigen Binding Fragment Thereof and Use of Same in Tumor Treatment" filed on Dec. 29, 2017, the disclosures of which are hereby incorporated by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is 72331_Sequence_Listing_Revised_final_20210119.txt. The text file is 46 KB; was created on Jan. 19, 2021, contains no new matter, and is being submitted via EFS Web.

TECHNICAL FIELD

The present disclosure relates to an antibody, in particular to an isolated antibody or antigen binding fragment thereof and use of same in tumor treatment.

BACKGROUND ART

Human OX40 is a protein consisting of 277 amino acids with an apparent molecular weight of approximately 50 kD due to the glycosylations at positions N146 and N160 [1,2]. OX40 is a type I transmembrane protein, with an extracellular segment that can bind to its natural ligand OX40L (CD252), and an intracellular segment that is coupled to multiple signaling pathways activated by T cells.

Human OX40 is mainly expressed on activated T cells, including CD4, CD8, Th, Treg cells, and the like (reviewed in [3]). The expression of OX40 is very low on naïve T cells, but after an antigen-induced stimulation, its expression level is up-regulated and reaches a peak within 12 h to 5-6 days. Similarly, the expression of OX40L is also affected by the state of cell activation [3]. OX40L expression can be detected in APC cells 1-3 days after antigen stimulation. Interestingly, in addition to immune cells, muscle cells can also express OX40L under the stimulation of inflammatory factors [4, 5], suggesting that OX40L-OX40 signaling pathway may widely act on the inflammatory response of organisms.

Based on the characteristics that OX40/OX40L is mainly expressed in antigen-activated T cells, OX40 agonists are developed and expected to become an immunotherapy with strong specificity and low side effects.

The activation of antigen-dependent OX40L/OX40 costimulatory molecules is coupled to multiple signaling pathways in T cells. A crystal structure study indicates that binding of OX40L and OX40 can induce trimerization of OX40-OX40L complex [6], thereby forming the intracellular binding sites of receptor-associated factor (TRAF). The latter (TRAF2, 5) can in turn activate NF-κB signaling pathway and inhibit T cell apoptosis [5, 7, 8]. A study found that activation of OX40 can lead to high expression of Bcl-2 and Bcl-xL [9], suggesting that OX40 may induce the expression of anti-apoptotic proteins through NF-κB signaling pathway to achieve its function of inhibiting T cell apoptosis.

PKB/PI3K is another important signaling pathway downstream from OX40. The studies found that on the one hand, the costimulatory signal of OX40 on T cells is essential to maintain PKB activation; on the other hand, constitutively activated PKB can antagonize the down-regulation of anti-apoptotic proteins in T cells caused by OX40 deficiency [10]. An OX40 costimulatory signal can maintain the expression of Survivin through PKB/PI3K signaling pathway [11].

Finally, the activation of TCR and OX40 on T cells can also synergistically induce calcium flow and the activation of NFAT signaling pathway, regulating the expression of cytokines including IL-2, IL-4, IL-5 and IFN-γ [12].

In summary, the above studies indicate that the activation of OX40 can regulate the proliferation, apoptosis and cytokine secretion activity of T cells through NF-κB signaling pathway, PKB/PI3K signaling pathway and NFAT signaling pathway, thereby achieving the effect of enhancing the vitality of the immune system.

However, a more in-depth study of OX40 found that as a subpopulation of $CD4^+$ cells, Treg cells can also express OX40. OX40 is continuously expressed on mouse Treg cells, while its expression on human Treg cells is up-regulated after activation [13, 14]. Treg is a type of cells that have an inhibitory effect on effector T cells (Teff), so it is very interesting to study the function of OX40 on Treg cells. The existing evidences show that OX40 signaling pathway has little effect on the development of natural Treg (nTreg), while most studies show that it has a relatively clear inhibitory regulatory effect on the development of induced Treg (iTreg) (reviewed in [3, 15]).

Different from the clear conclusion about OX40 signaling pathway in the development of Treg cells, the studies on the regulatory effect of OX40 signaling pathway on the functions of Treg cells are inconsistent. Some studies indicate that OX40 signaling pathway can inhibit the immunosuppressive function of Treg cells [14, 16-20], while others found that OX40 is essential for Treg cells to fully exert their immunosuppressive function [21-23]. This inconsistency may be related to the different experimental models and experimental conditions adopted by the different laboratories, and also suggest that the functions of OX40 on Treg cells in organisms may be affected by different physiological and pathological conditions.

Similarly, the effects of OX40 activity on the proliferation and apoptosis of Treg cells also vary among the microenvironments around the cells. For example, in the absence of IFN-γ and IL-4 [24] or in the presence of FoxP3 expression [17], the activation of OX40 can significantly promote the amplification of Treg cells. However, in other cases, this OX40-dependent Treg amplification is not observed [14].

In summary, the regulation of OX40 to the immune system is a complex process. On the one hand, OX40 costimulatory signal can in some cases achieve the effect of immune activation through a dual mechanism of enhancing the activity of effector T cells and inhibiting Treg function; on the other hand, OX40 signaling pathway may also promote the proliferation of Treg cells and antagonize the function of effector T cells. In addition, the action mechanism of ADCC can clear both Teff cells and negatively regulated Treg cells.

Tumor infiltrating lymphocytes (TILs) are the lymphocytes that migrate from the peripheral lymphatic system and are detained inside tumor tissue, the number and type of which are often related to the prognosis of patients [25, 26]. Many studies show that OX40 is highly expressed on tumor infiltrating lymphocytes, especially Treg [27-32], which may probably be a manifestation of the activation of T cells by a tumor-specific antigen. In lymphoma, due to the significant up-regulation of OX40 on Treg, OX40 can even be used as a biomarker for antigen-specific Treg [30]. Interestingly, the expression of OX40 is related to the clinical prognosis of patients with tumor. In colon cancer, the high expression of OX40 on TIL, mesenteric lymph nodes, or lymph nodes at the edge of the tumor is associated with a longer survival time [31]. Similarly, in the patients with melanoma, the number of OX40-positive cells in TIL and tumor peripheral lymphocytes is related to the metastasis of tumor and survival time of patients [32].

Based on the above findings and the important role of OX40 in T cell activation, OX40 has become an important target for tumor treatment. The activation of OX40 signaling pathway can be achieved by using an activated OX40 antibody or binding to an OX40L fusion protein, etc. The earliest attempt of tumor treatment using an OX40 agonist can be traced back to 2000, and Weinberg's laboratory reported that intraperitoneal administration of OX40L: Ig fusion protein can prevent the tumor formation of subcutaneous xenografts [33]. Interestingly, the mice in the treatment group still have a good immunity to the inoculation of same tumor again, but no similar immunity to the inoculation of different tumor cells [33]. This result suggests that OX40 agonists can enhance tumor-specific memory T cell responses during tumor treatment. At the same time, the studies further indicate that both CD4+ and CD8+ cells are necessary for the antitumor activities of OX40 agonists [33, 34]. Since then, many preclinical studies have proved that use of OX40 agonist alone or in combination with other tumor therapies in animal models can effectively inhibit tumor growth and even prevent tumor recurrence (reviewed in [15, 35]).

MAIN REFERENCES

1. Mallett S, Fossum S, Barclay A N. Characterization of the MRC OX40 antigen of activated CD4 positive T lymphocytes—a molecule related to nerve growth factor receptor. EMBO J. 1990; 9: 1063-8. doi:
2. Byun M, Ma C S, Akcay A, Pedergnana V, Palendira U, Myoung J, Avery D T, Liu Y, Abhyankar A, Lorenzo L, Schmidt M, Lim H K, Cassar 0, et al. Inherited human OX40 deficiency underlying classic Kaposi sarcoma of childhood. J Exp Med. 2013; 210: 1743-59. doi: 10.1084/jem.20130592.
3. Willoughby J, Griffiths J, Tews I, Cragg M S. OX40: Structure and function-What questions remain? Mol Immunol. 2017; 83: 13-22. doi: 10.1016/j.molimm.2017.01.006.
4. Burgess J K, Carlin S, Pack R A, Arndt G M, Au W W, Johnson P R, Black J L, Hunt N H. Detection and characterization of OX40 ligand expression in human airway smooth muscle cells: a possible role in asthma? J Allergy Clin Immunol. 2004; 113: 683-9. doi: 10.1016/j.jaci.2003.12.311.
5. Imura A, Hori T, Imada K, Ishikawa T, Tanaka Y, Maeda M, Imamura S, Uchiyama T. The human OX40/gp34 system directly mediates adhesion of activated T cells to vascular endothelial cells. J Exp Med. 1996; 183: 2185-95. doi:
6. Compaan D M, Hymowitz S G. The crystal structure of the costimulatory OX40-OX40L complex. Structure. 2006; 14: 1321-30. doi: 10.1016/j.str.2006.06.015.
7. Song J, So T, Croft M. Activation of NF-kappaB 1 by OX40 contributes to antigen-driven T cell expansion and survival. J Immunol. 2008; 180: 7240-8. doi:
8. Croft M. Control of immunity by the TNFR-related molecule OX40 (CD134). Annu Rev Immunol. 2010; 28: 57-78. doi: 10.1146/annurev-immunol-030409-101243.
9. Rogers P R, Song J, Gramaglia I, Killeen N, Croft M. OX40 promotes Bcl-xL and Bcl-2 expression and is essential for long-term survival of CD4 T cells. Immunity. 2001; 15: 445-55. doi:
10. Song J, Salek-Ardakani S, Rogers P R, Cheng M, Van Parijs L, Croft M. The costimulation-regulated duration of PKB activation controls T cell longevity. Nat Immunol. 2004; 5: 150-8. doi: 10.1038/ni1030.
11. Song J, So T, Cheng M, Tang X, Croft M. Sustained survivin expression from OX40 costimulatory signals drives T cell clonal expansion. Immunity. 2005; 22: 621-31. doi: 10.1016/j.immuni.2005.03.012.
12. So T, Song J, Sugie K, Altman A, Croft M. Signals from OX40 regulate nuclear factor of activated T cells cl and T cell helper 2 lineage commitment. Proc Natl Acad Sci USA. 2006; 103: 3740-5. doi: 10.1073/pnas.0600205103.
13. So T, Croft M. Cutting edge: OX40 inhibits TGF-beta- and antigen-driven conversion of naive CD4 T cells into CD25+Foxp3+ T cells. J Immunol. 2007; 179: 1427-30. doi:
14. Vu M D, Xiao X, Gao W, Degauque N, Chen M, Kroemer A, Killeen N, Ishii N, Li X C. OX40 costimulation turns off Foxp3+Tregs. Blood. 2007; 110: 2501-10. doi: 10.1182/blood-2007-01-070748.
15. Aspeslagh S, Postel-Vinay S, Rusakiewicz S, Soria J C, Zitvogel L, Marabelle A. Rationale for anti-OX40 cancer immunotherapy. Eur J Cancer. 2016; 52: 50-66. doi: 10.1016/j.ejca.2015.08.021.
16. Xiao X, Gong W, Demirci G, Liu W, Spoerl S, Chu X, Bishop D K, Turka L A, Li X C. New insights on OX40 in the control of T cell immunity and immune tolerance in vivo. J Immunol. 2012; 188: 892-901. doi: 10.4049/jimmunol.1101373.
17. Kroemer A, Xiao X, Vu M D, Gao W, Minamimura K, Chen M, Maki T, Li X C. OX40 controls functionally different T cell subsets and their resistance to depletion therapy. J Immunol. 2007; 179: 5584-91. doi:
18. Valzasina B, Guiducci C, Dislich H, Killeen N, Weinberg A D, Colombo M P. Triggering of OX40 (CD134) on CD4(+)CD25+ T cells blocks their inhibitory activity: a novel regulatory role for OX40 and its comparison with GITR. Blood. 2005; 105: 2845-51. doi: 10.1182/blood-2004-07-2959.
19. Piconese S, Valzasina B, Colombo M P. OX40 triggering blocks suppression by regulatory T cells and facilitates tumor rejection. J Exp Med. 2008; 205: 825-39. doi: 10.1084/jem.20071341.
20. Voo K S, Bover L, Harline M L, Vien L T, Facchinetti V, Arima K, Kwak L W, Liu Y J. Antibodies targeting human OX40 expand effector T cells and block inducible and natural regulatory T cell function. J Immunol. 2013; 191: 3641-50. doi: 10.4049/jimmuno1.1202752.
21. Takeda I, Ine S, Killeen N, Ndhlovu L C, Murata K, Satomi S, Sugamura K, Ishii N. Distinct roles for the OX40-OX40 ligand interaction in regulatory and non-regulatory T cells. J Immunol. 2004; 172: 3580-9. doi:
22. Piconese S, Pittoni P, Burocchi A, Gorzanelli A, Care A, Tripodo C, Colombo M P. A non-redundant role for OX40 in the competitive fitness of Treg in response to IL-2. Eur J Immunol. 2010; 40: 2902-13. doi: 10.1002/ej i 0.201040505.
23. Griseri T, Asquith M, Thompson C, Powrie F. OX40 is required for regulatory T cell-mediated control of colitis. J Exp Med. 2010; 207: 699-709. doi: 10.1084/jem.20091618.
24. Ruby C E, Yates M A, Hirschhorn-Cymerman D, Chlebeck P, Wolchok J D, Houghton A N, Offner H, Weinberg A D. Cutting Edge: OX40 agonists can drive regulatory T cell expansion if the cytokine milieu is right. J Immunol. 2009; 183: 4853-7. doi: 10.4049/jimmuno1.0901112.
25. Zhang L, Conejo-Garcia J R, Katsaros D, Gimotty P A, Massobrio M, Regnani G, Makrigiannakis A, Gray H, Schlienger K, Liebman M N, Rubin S C, Coukos G. Intratumoral T cells, recurrence, and survival in epithelial ovarian cancer. N Engl J Med. 2003; 348: 203-13. doi: 10.1056/NEJMoa020177.
26. Galon J, Costes A, Sanchez-Cabo F, Kirilovsky A, Mlecnik B, Lagorce-Pages C, Tosolini M, Camus M, Berger A, Wind P, Zinzindohoue F, Bruneval P, Cugnenc P H, et al. Type, density, and location of immune cells within human colorectal tumors predict clinical outcome. Science. 2006; 313: 1960-4. doi: 10.1126/science.1129139.
27. Sarff M, Edwards D, Dhungel B, Wegmann K W, Corless C, Weinberg A D, Vetto J T. OX40 (CD134) expression in sentinel lymph nodes correlates with prognostic features of primary melanomas. Am J Surg. 2008; 195: 621-5; discussion 5. doi: 10.1016/j.amjsurg.2007.12.036.
28. Xie F, Wang Q, Chen Y, Gu Y, Mao H, Zeng W, Zhang X. Costimulatory molecule OX40/OX40L expression in ductal carcinoma in situ and invasive ductal carcinoma of breast: an immunohistochemistry-based pilot study. Pathol Res Pract. 2010; 206: 735-9. doi: 10.1016/j.prp.2010.05.016.
29. Vetto J T, Lum S, Morris A, Sicotte M, Davis J, Lemon M, Weinberg A. Presence of the T-cell activation marker OX-40 on tumor infiltrating lymphocytes and draining lymph node cells from patients with melanoma and head and neck cancers. Am J Surg. 1997; 174: 258-65. doi:
30. Marabelle A, Kohrt H, Sagiv-Barfi I, Ajami B, Axtell R C, Zhou G, Rajapaksa R, Green M R, Torchia J, Brody J, Luong R, Rosenblum M D, Steinman L, et al. Depleting tumor-specific Tregs at a single site eradicates disseminated tumors. J Clin Invest. 2013; 123: 2447-63. doi: 10.1172/JCI64859.
31. Petty J K, He K, Corless C L, Vetto J T, Weinberg A D. Survival in human colorectal cancer correlates with expression of the T-cell costimulatory molecule OX-40 (CD134). Am J Surg. 2002; 183: 512-8. doi:
32. Ladanyi A, Somlai B, Gilde K, Fejos Z, Gaudi I, Timar J. T-cell activation marker expression on tumor-infiltrating lymphocytes as prognostic factor in cutaneous malignant melanoma. Clin Cancer Res. 2004; 10: 521-30. doi:
33. Weinberg A D, Rivera M M, Prell R, Morris A, Ramstad T, Vetto J T, Urba W J, Alvord G, Bunce C, Shields J. Engagement of the OX-40 receptor in vivo enhances antitumor immunity. J Immunol. 2000; 164: 2160-9. doi:
34. Kjaergaard J, Tanaka J, Kim J A, Rothchild K, Weinberg A, Shu S. Therapeutic efficacy of OX-40 receptor antibody depends on tumor immunogenicity and anatomic site of tumor growth. Cancer Res. 2000; 60: 5514-21. doi:
35. Linch S N, McNamara M J, Redmond W L. OX40 Agonists and Combination Immunotherapy: Putting the Pedal to the Metal. Front Oncol. 2015; 5: 34. doi: 10.3389/fonc.2015.00034.

DISCLOSURE OF THE INVENTION

In order to overcome the problems in the prior art, the present disclosure provides new anti-human OX40 monoclonal antibodies and encoding polynucleotides thereof, and use of the same in tumor treatment.

The present disclosure provides an isolated antibody or antigen binding fragment thereof, comprising a heavy chain complementary determining region and a light chain complementary determining region, wherein the heavy chain complementary determining region is selected from one or more of the following sequences: SEQ ID NO: 1, SEQ ID NO: 2, SEQ ID NO: 3, SEQ ID NO: 7, SEQ ID NO: 9, SEQ ID NO: 10 and SEQ ID NO: 11.

Wherein, the heavy chain complementary determining region is: SEQ ID NO: 1, SEQ ID NO: 2 and/or SEQ ID NO: 3; SEQ ID NO: 1, SEQ ID NO: 7 and/or SEQ ID NO: 3; or SEQ ID NO: 9, SEQ ID NO: 10 and/or SEQ ID NO: 11.

Wherein, the light chain complementary determining region is selected from one or more of the following sequences: SEQ ID NO: 4, SEQ ID NO: 5, SEQ ID NO: 6, SEQ ID NO: 8, SEQ ID NO: 12, SEQ ID NO: 13 and SEQ ID NO: 14.

Wherein, the light chain complementary determining region is: SEQ ID NO: 4, SEQ ID NO: 5 and/or SEQ ID NO: 6; SEQ ID NO: 4, SEQ ID NO: 5 and/or SEQ ID NO: 8; or SEQ ID NO: 12, SEQ ID NO: 13 and/or SEQ ID NO: 14.

Wherein, the heavy chain complementary determining region comprises SEQ ID NO: 1, SEQ ID NO: 2 and SEQ ID NO: 3, and the light chain complementary determining region comprises SEQ ID NO: 4, SEQ ID NO: 5 and SEQ ID NO: 6; the heavy chain complementary determining region comprises SEQ ID NO: 1, SEQ ID NO: 7 and SEQ ID NO: 3, and the light chain complementary determining region comprises SEQ ID NO: 4, SEQ ID NO: 5 and SEQ ID NO: 6; the heavy chain complementary determining region comprises SEQ ID NO: 1, SEQ ID NO: 2 and SEQ ID NO: 3, and the light chain complementary determining region comprises SEQ ID NO: 4, SEQ ID NO: 5 and SEQ ID NO: 8; the heavy chain complementary determining region comprises SEQ ID NO: 1, SEQ ID NO: 7 and SEQ ID NO: 3, and the light chain complementary determining region comprises SEQ ID NO: 4, SEQ ID NO: 5 and SEQ ID NO: 8; or the heavy chain complementary determining region comprises SEQ ID NO: 9, SEQ ID NO: 10 and SEQ ID NO: 11, and the light chain complementary determining region comprises SEQ ID NO: 12, SEQ ID NO: 13 and SEQ ID NO: 14.

Wherein, the heavy chain variable region may be replaced with the following sequences: SEQ ID NO: 15, SEQ ID NO: 17, SEQ ID NO: 19, or SEQ ID NO: 29.

Wherein, the light chain variable region may be replaced with the following sequences: SEQ ID NO: 16, SEQ ID NO: 18, SEQ ID NO: 20, or SEQ ID NO: 30.

Wherein, the heavy chain variable region comprises SEQ ID NO: 15, and the light chain variable region comprises SEQ ID NO: 16; the heavy chain variable region comprises SEQ ID NO: 17, and the light chain variable region comprises SEQ ID NO: 16; the heavy chain variable region comprises SEQ ID NO: 15, and the light chain variable region comprises SEQ ID NO: 18; the heavy chain variable region comprises SEQ ID NO: 17, and the light chain variable region comprises SEQ ID NO: 18; the heavy chain variable region comprises SEQ ID NO: 19, and the light chain variable region comprises SEQ ID NO: 20; or the heavy chain variable region comprises SEQ ID NO: 29, and the light chain variable region comprises SEQ ID NO: 30.

Wherein, the antibody or antigen binding fragment thereof is a humanized or fully human monoclonal antibody.

Wherein, the antibody or antigen binding fragment thereof is a camelized single domain antibody, a bifunctional antibody, a scFv, a scFv dimer, a BsFv, a dsFv, a dsFv2, a dsFv-dsFv', an Fv fragment, an Fab, an Fab', an F(ab')2, a ds bifunctional antibody, a nanobody, a domain antibody or a bivalent domain antibody.

Wherein, the antibody or antigen binding fragment thereof further comprises an immunoglobulin constant region, which includes a constant region of human IgG1, IgG2, or IgG4 protein.

The antibody or antigen binding fragment thereof provided by the present disclosure further comprises a conjugate.

The present disclosure provides an isolated polynucleotide encoding the antibody or antigen binding fragment thereof.

The present disclosure provides a vector comprising the isolated polynucleotide.

The present disclosure provides a host cell comprising the vector.

The present disclosure provides a method for expressing the antibody or antigen binding fragment thereof, which comprises culturing the host cell under conditions for expression of the isolated polynucleotide.

The present disclosure also provides a kit comprising the antibody or antigen binding fragment thereof.

The present disclosure also provides a pharmaceutical composition comprising the antibody or antigen binding fragment thereof and one or more pharmaceutically acceptable carriers.

The present disclosure provides use of the antibody or antigen binding fragment thereof in the detection of the presence or level of human or monkey OX40.

The present disclosure provides use of the antibody or antigen binding fragment thereof in the detection and identification of an individual suffering from a disorder or a condition responsive to an OX40 agonist.

The present disclosure provides use of the antibody or antigen binding fragment thereof in the monitoring of the therapeutic response or disease progression during an OX40 agonist treatment.

The present disclosure provides use of the antibody or antigen binding fragment thereof in the preparation of a medicament for treating a condition that would benefit from an up-regulated immune response. Wherein, the condition is cancer or chronic viral infection.

The present disclosure provides a method for detecting the presence or level of human or monkey OX40, comprising using the antibody or antigen binding fragment thereof of the present disclosure.

The present disclosure provides a method for detecting and identifying an individual suffering from a disorder or a condition that is responsive to an OX40 agonist, comprising using the antibody or antigen binding fragment of the present disclosure.

The present disclosure provides a method for monitoring the therapeutic response or disease progression during an OX40 agonist treatment, comprising using the antibody or antigen binding fragment thereof of the present disclosure.

The present disclosure provides a method for treating a condition that would benefit from an up-regulated immune response, comprising using the antibody or antigen binding fragment of the present disclosure. Wherein, the condition is cancer or chronic viral infection.

The present disclosure provides an antibody or antigen binding fragment thereof for detecting the presence or level of human or monkey OX40.

The present disclosure provides an antibody or antigen binding fragment for detecting and identifying an individual suffering from a disorder or a condition responsive to an OX40 agonist.

The present disclosure provides an antibody or antigen binding fragment thereof for monitoring the therapeutic response or disease progression during an OX40 agonist treatment.

The present disclosure provides an antibody or antigen binding fragment thereof for treating a condition that would benefit from an up-regulated immune response. Wherein, the condition is cancer or chronic viral infection.

Compared with the prior art, the present disclosure has the following beneficial effects: the inventors developed human-mouse chimeric anti-OX40 monoclonal antibodies by modifying independently developed mouse-derived anti-OX40 antibodies, and the antibodies of the present disclosure can bind to the OX40 protein on the cell surface, activate its downstream signaling pathways and activate the functions of T cells, thereby providing a potential for treating tumor or chronic viral infection.

BEST MODES FOR CARRYING OUT THE INVENTION

Figure 1:
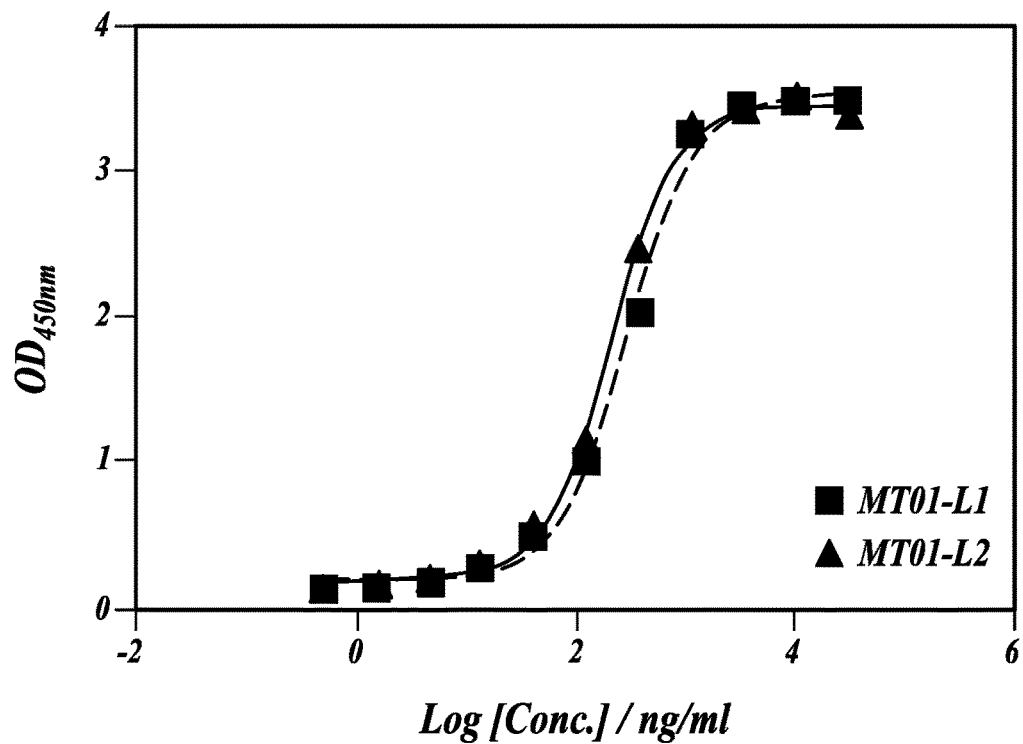
FIG. 1 shows the results of ELISA binding assay.

The following description of the present disclosure is merely intended to illustrate various embodiments of the present disclosure. As such, the specific modifications discussed herein should not be construed as limitations to the scope of the disclosure. It will be apparent to those skilled in the art that various equivalents, changes and modifications may be made without departing from the scope of the present disclosure, and it should be understood that such equivalent embodiments are included in the scope of the present disclosure. All references cited herein, including publications, patents and patent applications, are incorporated herein by reference in their entirety.

Terminology

The term "antibody" as used herein includes any immunoglobulin, monoclonal antibody, polyclonal antibody, multispecific antibody, or bispecific (bivalent) antibody that can bind to a specific antigen. A native intact antibody comprises two heavy chains and two light chains. Each heavy chain consists of a variable region and the first, second, and third constant regions, while each light chain consists of a variable region and a constant region. Mammalian heavy chains can be classified as α, δ, ε, γ and μ, and mammalian light chains can be classified as λ or κ. An antibody has a "Y" shape, with the stem of the Y shape structure consisting of the second and third constant regions of two heavy chains bound together via disulfide bonds. Each arm of the Y shape structure comprises the variable region and the first constant region of one heavy chain, which is bound to the variable and constant regions of one light chain. The variable regions of the light and heavy chains determine the binding of antigen. The variable region of each chain contains three hypervariable regions called the complementary determining regions (CDRs). The CDRs of light chain (L) comprise LCDR1, LCDR2, and LCDR3, and the CDRs of heavy chain (H) comprise HCDR1, HCDR2 and HCDR3. The CDR boundaries of the antibodies or antigen binding fragments in the present disclosure may be named or identified by the nomenclature of Kabat, IMGT, Chothia, or Al-Lazikani (Al-Lazikani, B., Chothia, C., Lesk, A. M., J. Mol. Biol., 273(4), 927(1997); Chothia, C. et al., J Mol Biol. 186(3): 651-63(1985); Chothia, C. and Lesk, A. M., J. Mol. Biol., 196, 901(1987); Chothia, C. et al., Nature. December 21-28; 342(6252): 877-83(1989); Kabat E. A. et al., National Institutes of Health, Bethesda, Md. (1991)). The three CDRs are interposed between flanking stretches known as framework regions (FRs), which are more highly conservative than the CDRs and form a scaffold to support the hypervariable loops. The constant regions of the heavy and light chains are not involved in antigen binding, but have various effector functions. Antibodies can be assigned to several classes based on the amino acid sequences of the constant regions of their heavy chains. The five major classes or isotypes of antibodies are IgA, IgD, IgE, IgG, and IgM, which are characterized by the presence of α, δ, ε, γ and μ heavy chains, respectively. Several of the major antibody classes are further divided into subclasses, such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain), etc.

The term "antigen binding fragment" as used herein refers to an antibody fragment formed from a portion of an antibody comprising one or more CDRs, or any other antibody fragment that binds to an antigen but does not have an intact antibody structure. Examples of antigen binding fragment include, without limitation, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a bivalent single-chain antibody (BsFv), a multispecific antibody, a camelized single domain antibody, a nanobody, a domain antibody, and a bivalent domain antibody. An antigen binding fragment is capable of binding to the same antigen to which the parent antibody binds. In certain embodiments, the antigen binding fragments may comprise one or more CDRs from a particular human antibody grafted to a framework region from one or more different human antibodies.

The "Fab" fragment of an antibody refers to a portion of the antibody molecular consisting of a light chain (comprising both variable and constant regions) bound to the variable region and a portion of constant region of a heavy chain via disulfide bonds.

The term "Fab'" fragment refers to a Fab fragment that comprises a portion of hinge region.

The term "F (ab')2" refers to a dimer of Fabs.

The Fc portion of an antibody is responsible for various effector functions, such as ADCC and CDC, but is not involved in binding to an antigen.

The "Fv" fragment of an antibody refers to the smallest fragment of an antibody that contains a complete antigen binding site. An Fv fragment consists of the variable region of a light chain and the variable region of a heavy chain.

The term "single-chain Fv antibody" or "scFv" refers to an engineered antibody formed by a light chain variable region and a heavy chain variable region connected to one another directly or via a peptide chain (Huston J S et al., Proc Natl Acad Sci USA, 85: 5879 (1988)).

The term "single-chain antibody Fv-Fc" or "scFv-Fc" refers to an engineered antibody consisting of a scFv connected to the Fc region of a certain antibody.

The term "camelized single domain antibody", "heavy chain antibody", or "heavy-chain-only antibody (HCAb)" refers to an antibody that contains two VH domains but no light chain (Riechmann L. and Muyldermans S., J Immunol Methods. 231(1-2): 25-38(1999); Muyldermans S., J Biotechnol. 74(4): 277-302 (2001); WO94/04678; WO94/25591; U.S. Pat. No. 6,005,079). Heavy chain antibodies were originally derived from Camelidae (camels, dromedaries, and llamas). Despite lack of light chains, camelized antibodies have an authentic antigen-binding repertoire (Hamers-Casterman C. et al., Nature 363(6428): 446-8 (1993); Nguyen V K. et al., Heavy-chain antibodies in Camelidae: a case of evolutionary innovation, Immunogenetics. 54 (1): 39-47(2002); Nguyen V K. et al., Immunology. 109(1): 93101 (2003)). The variable domain (VH domain) of a heavy chain antibody is the smallest known antigen-binding unit for generating adaptive immunity (Koch-Nolte et al., FASEB J. 21(13): 3490-8. Epub (2007)).

The term "nanobody" refers to an antibody fragment that consists of one VH domain and two constant domains CH2 and CH3 from a heavy chain antibody.

The term "diabody" comprises a small antibody fragment with two antigen-binding sites, wherein the fragment comprises a VH domain connected to a VL domain on the same polypeptide chain (see, e.g., Holliger P. et al., Proc Natl Acad Sci USA. 90(14): 6444-8(1993); EP404097; WO93/11161). The linker between the two domains is too short to allow pairing between the two domains on the same chain, thereby forcing the two domains to pair with the complementary domains of another chain to form two antigen-binding sites. The two antigen-binding sites may target and bind the same or different antigens (or antigen epitopes).

The term "domain antibody" refers to an antibody fragment containing only one heavy chain variable region or one light chain variable region. In certain instances, two or more VH domains are covalently joined with a polypeptide linker to form a bivalent domain antibody. The two VH domains of a bivalent domain antibody may target and act on the same or different antigens.

In certain embodiments, the "(dsFv)2" comprises three peptide chains: two VH moieties are linked by a polypeptide linker and connected to two VL moieties by disulfide bridges.

In certain embodiments, the "bispecific ds diabodies" comprise VH1-VL2 (linked by a polypeptide linker) and VL1-VH2 (also linked by a polypeptide linker), both of which are connected via a disulfide bond between VH1 and VL1.

A "bispecific dsFv" or "dsFv-dsFv" comprises three polypeptide chains: a VH1-VH2 moiety, the heavy chains of which are linked by a polypeptide linker (e.g., a long flexible linker) and connected to VL1 and VL2 moieties via disulfide bonds, respectively, wherein each pair of heavy chain and light chain paired with disulfide bonds has a different antigen specificity.

In certain embodiments, the "scFv dimers" are bivalent diabodies or bivalent single chain antibodies (BsFv) comprising two VH-VL moieties (linked by a polypeptide linker) which are dimerized, wherein the VHs from two moieties coordinate with the VLs from another moiety to form two binding sites, which can target and bind to the same antigen (or epitope) or different antigens (or epitopes). In other embodiments, the "scFv dimers" are bispecific diabodies comprising $V_{L1}$-$V_{H2}$ (linked by a polypeptide linker) and $V_{H1}$—$V_{L2}$ (linked by a peptide linker) connected to each other, wherein $V_{HA}$ coordinates with $V_{L1}$ and $V_{H2}$ coordinates with $V_{L2}$, and each coordinated pair has a different antigen specificity.

The term "fully human" as used herein with respect to an antibody or antigen binding fragment means that the antibody or antigen binding fragment has or consists of a certain amino acid sequence which corresponds to the amino acid sequence of an antibody produced by human or a human immune cell, or an antibody derived from a non-human source, such as a transgenic non-human animal using a human antibody library, or corresponds to other sequence encoding a human antibody. In certain embodiments, the fully human antibodies do not contain an amino acid residue (particularly an antigen binding residue) derived from a non-human antibody.

The term "humanized" as used herein with respect to an antibody or antigen binding fragment refers to an antibody or antigen-binding fragment comprising a CDR derived from a non-human animal, a FR region derived from human, and when applicable, a constant region derived from human. Because humanized antibodies or antigen binding fragments have a reduced immunogenicity, they can be used as a therapeutic agent for human in certain embodiments. In some embodiments, the non-human animals are mammals, such as a mouse, a rat, a rabbit, a goat, a sheep, a guinea pig, or a hamster. In some embodiments, the humanized antibodies or antigen binding fragments consist essentially of human sequences except that the CDR sequences are non-human. In some embodiments, the human-derived FR regions may comprise the same amino acid sequence as the human antibodies from which they are derived, or they may comprise some amino acid changes, for example, no more than 10, 9, 8, 7, 6, 5, 4, 3, 2 or 1 amino acid change(s). In some embodiments, the amino acid change(s) may be present only in the heavy chain FR region, only in the light chain FR region, or in both the chains. In some preferred embodiments, the humanized antibodies comprise human FR1-3, and human JH and JK.

The term "chimeric" as used herein means an antibody or antigen binding fragment having a portion of heavy and/or light chain derived from one species, and the rest of the heavy and/or light chain derived from a different species. In an illustrative example, the chimeric antibody may comprise a constant region derived from human and a variable region from a non-human animal, such as a mouse.

The term "OX40" refers to a receptor that binds to OX40L. It is a type I membrane protein belonging to the TNF receptor family. Other names are ACT-4, OX40L receptor, CD134 antigen, ACT35 antigen, and TNFRSF4. It has a molecular weight of 50 kDa and is stored in SwissProt under the registration number P43489.

As used herein, an "anti-OX40 antibody" refers to an antibody that can specifically bind to OX40 (e.g., human or monkey OX40) with an affinity sufficient to provide a diagnostic and/or therapeutic use.

The term "specific binding" or "specifically binds" as used herein refers to a non-random binding reaction between two molecules, such as a reaction between an antibody and an antigen. In certain embodiments, the antibodies or their antigen binding fragments of the present disclosure specifically bind to human and/or monkey OX40 with a binding affinity ($K_D$) of $\leq 10^{-6}$ M. $K_D$ used in the present disclosure refers to the ratio of the dissociation rate to the association rate ($k_{off}/k_{on}$), which may be determined by the surface plasmon resonance method, for example using an instrument from such as Biacore.

As used herein, "MT01-L1" refers to a human-mouse chimeric monoclonal antibody having a heavy chain variable region shown in SEQ ID NO: 15, a light chain variable region shown in SEQ ID NO: 16, and a human-derived IgG1/κ isotype constant region.

As used herein, "MT01-L1(M1)" refers to a human-mouse chimeric monoclonal antibody having a heavy chain variable region shown in SEQ ID NO: 17, a light chain variable region shown in SEQ ID NO: 16, and a human-derived IgG1/κ isotype constant region.

As used herein, "MT01-L1(M2)" refers to a human-mouse chimeric monoclonal antibody having a heavy chain variable region shown in SEQ ID NO: 15, a light chain variable region shown in SEQ ID NO: 18, and a human-derived IgG1/κ isotype constant region.

As used herein, "MT01-L1(M1/M2)" refers to a human-mouse chimeric monoclonal antibody having a heavy chain variable region shown in SEQ ID NO: 17, a light chain variable region shown in SEQ ID NO: 18, and a human-derived IgG1/κ isotype constant region.

As used herein, "MT01-L1(G2)" refers to a human-mouse chimeric monoclonal antibody having a heavy chain variable region shown in SEQ ID NO: 15, a light chain variable region shown in SEQ ID NO: 16, and a human-derived IgG2/κ isotype constant region.

As used herein, "MT01-L2" refers to a human-mouse chimeric monoclonal antibody having a heavy chain variable region shown in SEQ ID NO: 19, a light chain variable region shown in SEQ ID NO: 20, and a human-derived IgG1/λ, isotype constant region.

As used herein, "MT01-L2(G2)" refers to a human-mouse chimeric monoclonal antibody having a heavy chain variable region shown in SEQ ID NO: 19, a light chain variable region shown in SEQ ID NO: 20, and a human-derived IgG2/κ isotype constant region.

As used herein, "MT01-C1" refers to a humanized monoclonal antibody having a heavy chain variable region shown in SEQ ID NO: 29, a light chain variable region shown in SEQ ID NO: 30, and a human-derived IgG1/K isotype constant region.

As used herein, "MT01-C1(G2)" refers to a humanized monoclonal antibody having a heavy chain variable region shown in SEQ ID NO: 29, a light chain variable region shown in SEQ ID NO: 30, and a human-derived IgG2/κ isotype constant region.

The term "conservative substitution" as used herein with respect to an amino acid sequence refers to replacing an amino acid residue with another amino acid residue having a side chain with the similar physical and chemical properties. For example, a conservative substitution can be made among amino acid residues with a hydrophobic side chain (e.g., Met, Ala, Val, Leu, and Ile), a neutral hydrophilic side chain (e.g., Cys, Ser, Thr, Asn and Gln), an acidic side chain (e.g., Asp, Glu), a basic side chain (e.g., His, Lys, and Arg), or an aromatic side chain (e.g., Trp, Tyr, and Phe). As known in the art, a conservative substitution generally does not cause a significant change in the conformational structure of a protein, and therefore could retain the biological activity of the protein.

The term "percent of sequence identity" with respect to amino acid sequences (or nucleic acid sequences) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). A conservative substitution of the amino acid residue may or may not be considered as an identical residue. An alignment for the purpose of determining percent of amino acid (or nucleic acid) sequence identity can be achieved using publicly available tools in the art. Those skilled in the art may use the default parameters provided by the tool, or may adjust the parameters as appropriate according to the needs for alignment, for example, by selecting a suitable algorithm.

As used herein, the term "T cells" include CD4+ T cells, CD8+ T cells, T helper type 1 T cells, T helper type 2 T cells, T helper type 17 T cells, and suppressor T cells.

The term "effector function" as used herein refers to a biological activity attributable to the binding of Fc region of an antibody to its effectors, such as C1 complex and Fc receptor. Exemplary effector functions include complement-dependent cytotoxicity (CDC) induced by interaction of antibodies and C1q on the C1 complex; antibody-dependent cell-mediated cytotoxicity (ADCC) induced by binding of Fc regions of antibodies to Fc receptors on effector cells; and phagocytosis.

The term "cancer" or "cancerous condition" as used herein refers to any medical condition which is mediated by neoplastic or malignant cell growth, proliferation, or metastasis, and causes both solid cancers and non-solid cancers such as leukemia. The term "tumor" as used herein refers to a solid mass of neoplastic and/or malignant cells.

"Treating" or "treatment" of a certain condition includes preventing or alleviating a certain condition, slowing the rate at which a certain condition rises or develops, reducing the risk of developing a certain condition, preventing or delaying the development of symptoms associated with a certain condition, reducing or terminating symptoms associated with a certain condition, generating a complete or partial reversal of a certain condition, curing a certain condition, or a combination thereof. "Treating" or "treatment" with respect to a cancer may refer to inhibiting or slowing neoplastic or malignant cell growth, proliferation, or metastasis, or a certain combination thereof. "Treating" or "treatment" with respect to a tumor includes eradicating all or part of the tumor, inhibiting or slowing tumor growth and metastasis, preventing or delaying the development of the tumor, or a certain combination thereof.

An "isolated" substance has been artificially changed from its natural state. If an "isolated" substance or component occurs in nature, it has been changed or removed from its original state, or both. For example, a polynucleotide or a polypeptide naturally present in a living animal is not "isolated", but the same polynucleotide or polypeptide is considered as being "isolated" if it has been sufficiently separated from the coexisting materials in its natural state so as to exist in a sufficient pure state. In certain embodiments, the antibodies or antigen binding fragments have a purity of at least 90%, 93%, 95%, 96%, 97%, 98%, or 99%, as determined by electrophoretic methods (such as SDS-PAGE, isoelectric focusing, capillary electrophoresis), or chromatographic methods (such as ion exchange chromatography or reverse phase HPLC).

The term "vector" as used herein refers to a vehicle into which a polynucleotide encoding a certain protein may be operably inserted so as to bring about the expression of that protein. A vector may be used to transform, transduce, or transfect a host cell so as to bring about the expression of the genetic element it carries within the host cell. By way of example, vectors comprise plasmids, phagemids, cosmids, artificial chromosomes such as yeast artificial chromosome (YAC), bacterial artificial chromosome (BAC), or P1-derived artificial chromosome (PAC), bacteriophages such as λ phage or M13 phage, and animal viruses. The categories of animal viruses used as vectors comprise retrovirus (including lentivirus, adenovirus, adeno-associated virus, herpesvirus (e.g., herpes simplex virus), poxvirus, baculovirus, papillomavirus, and papovavirus (e.g., SV40)). A vector may contain a variety of elements for controlling expression, including a promoter sequence, a transcription initiation sequence, an enhancer sequence, a selectable element, and a reporter gene. In addition, a vector may contain an origin of replication. A vector may also comprise a component to aid in its entry into cell, including but not limited to a viral particle, a liposome, or a protein coat.

The term "host cell" as used herein refers to a cell into which an exogenous polynucleotide and/or a vector have/has been introduced.

The term "disease related to or associated to OX40" as used herein refers to any condition that is caused, exacerbated, or otherwise related due to an increase or decrease in OX40 expression or activity.

The term "therapeutically effective amount" or "effective dosage" as used herein refers to the dosage or concentration of a certain drug effective to treat a disease or a condition associated with OX40. For example, with regard to use of the antibodies or antigen binding fragments disclosed herein, a therapeutically effective amount is a dosage or a concentration at which the antibodies or antigen binding fragments are capable of eradicating all or a part of tumor, inhibiting or slowing tumor growth, inhibiting growth or proliferation of cells mediating a cancerous condition, inhibiting tumor cell metastasis, ameliorating any symptom or marker associated with a tumor or cancerous condition, preventing or delaying the development of a tumor or cancerous condition, or some combination thereof.

The term "pharmaceutically acceptable" refers to that the designated carrier, vehicle, diluent, excipient, and/or salt are/is generally chemically and/or physically compatible with the other ingredients in the formulation, and physiologically compatible with the recipient.

Regarding Anti-OX40 Antibodies

In certain embodiments, the present disclosure provides exemplary monoclonal antibodies MT01-L1, MT01-L1 (M1), MT01-L1(M2), MT01-L1(M1/M2), MT01-L1(G2), MT01-L2 and MT01-L2(G2), MT01-C1 and MT01-C1 (G2). Their CDR sequences are shown in Table 1, and the heavy chain or light chain complementary determining region sequences are also listed as follows:

TABLE 1

Sequence information of monoclonal antibodies

|  |  | CDR1 | CDR2 | CDR3 | Isotype |
|---|---|---|---|---|---|
| MT01-L1 | Heavy chain (SEQ ID NO: 21) | SEQ ID NO: 1 | SEQ ID NO: 2 | SEQ ID NO: 3 | G1 |
|  | Light chain (SEQ ID NO: 24) | SEQ ID NO: 4 | SEQ ID NO: 5 | SEQ ID NO: 6 | κ |
| MT01-L1 (M1) | Heavy chain (SEQ ID NO: 22) | SEQ ID NO: 1 | SEQ ID NO: 7 | SEQ ID NO: 3 | G1 |
|  | Light chain (SEQ ID NO: 24) | SEQ ID NO: 4 | SEQ ID NO: 5 | SEQ ID NO: 6 | κ |
| MT01-L1 (M2) | Heavy chain (SEQ ID NO: 21) | SEQ ID NO: 1 | SEQ ID NO: 2 | SEQ ID NO: 3 | G1 |
|  | Light chain (SEQ ID NO: 25) | SEQ ID NO: 4 | SEQ ID NO: 5 | SEQ ID NO: 8 | κ |
| MT01-L1 (M1/M2) | Heavy chain (SEQ ID NO: 22) | SEQ ID NO: 1 | SEQ ID NO: 7 | SEQ ID NO: 3 | G1 |
|  | Light chain (SEQ ID NO: 25) | SEQ ID NO: 4 | SEQ ID NO: 5 | SEQ ID NO: 8 | κ |
| MT01-L1 (G2) | Heavy chain (SEQ ID NO: 23) | SEQ ID NO: 1 | SEQ ID NO: 2 | SEQ ID NO: 3 | G2 |
|  | Light chain (SEQ ID NO: 24) | SEQ ID NO: 4 | SEQ ID NO: 5 | SEQ ID NO: 6 | κ |
| MT01-L2 | Heavy chain (SEQ ID NO: 26) | SEQ ID NO: 9 | SEQ ID NO: 10 | SEQ ID NO: 11 | G1 |
|  | Light chain (SEQ ID NO: 27) | SEQ ID NO: 12 | SEQ ID NO: 13 | SEQ ID NO: 14 | λ |
| MT01-L2 (G2) | Heavy chain (SEQ ID NO: 28) | SEQ ID NO: 9 | SEQ ID NO: 10 | SEQ ID NO: 11 | G2 |
|  | Light chain (SEQ ID NO: 27) | SEQ ID NO: 12 | SEQ ID NO: 13 | SEQ ID NO: 14 | λ |
| MT01-C1 | Heavy chain (SEQ ID NO: 31) | SEQ ID NO: 1 | SEQ ID NO: 2 | SEQ ID NO: 3 | G1 |
|  | Light chain (SEQ ID NO: 32) | SEQ ID NO: 4 | SEQ ID NO: 5 | SEQ ID NO: 6 | κ |
| MT01-C1 (G2) | Heavy chain (SEQ ID NO: 33) | SEQ ID NO: 1 | SEQ ID NO: 2 | SEQ ID NO: 3 | G2 |
|  | Light chain (SEQ ID NO: 32) | SEQ ID NO: 4 | SEQ ID NO: 5 | SEQ ID NO: 6 | κ |

In some embodiments, the anti-OX40 antibodies or antigen binding fragments thereof comprise a heavy chain complementary determining region sequence selected from the group consisting of SEQ ID NO: 1, 2, 3, 7, 9, 10, and 11. In some embodiments, the anti-OX40 antibodies or antigen binding fragments thereof comprise a light chain complementary determining region sequence selected from the group consisting of SEQ ID NO: 4, 5, 6, 8, 12, 13, and 14.

In some embodiments, the anti-OX40 antibodies or antigen binding fragments thereof comprise a heavy chain complementary determining region selected from the group consisting of: a heavy chain complementary determining region comprising SEQ ID NO: 1, SEQ ID NO: 2 and/or SEQ ID NO: 3; a heavy chain complementary determining region comprising SEQ ID NO: 1, SEQ ID NO: 7 and/or SEQ ID NO: 3; and a heavy chain complementary determining region comprising SEQ ID NO: 9, SEQ ID NO: 10 and/or SEQ ID NO: 11.

In some embodiments, the anti-OX40 antibodies or antigen binding fragments thereof comprise a light chain complementary determining region selected from the group consisting of: a light chain complementary determining region comprising SEQ ID NO: 4, SEQ ID NO: 5 and/or SEQ ID NO: 6; a light chain complementary determining region comprising SEQ ID NO: 4, SEQ ID NO: 5 and/or SEQ ID NO: 8; and a light chain complementary determining region comprising SEQ ID NO: 12, SEQ ID NO: 13 and/or SEQ ID NO: 14.

In some embodiments, the anti-OX40 antibodies or antigen binding fragment thereof comprise: a) a heavy chain complementary determining region comprising SEQ ID NO: 1, SEQ ID NO: 2 and/or SEQ ID NO: 3, and a light chain complementary determining region comprising SEQ ID NO: 4, SEQ ID NO: 5 and/or SEQ ID NO: 6; b) a heavy chain complementary determining region comprising SEQ ID NO: 1, SEQ ID NO: 7 and/or SEQ ID NO: 3, and a light chain complementary determining region comprising SEQ ID NO: 4, SEQ ID NO: 5 and/or SEQ ID NO: 6; c) a heavy chain complementary determining region comprising SEQ ID NO: 1, SEQ ID NO: 2 and/or SEQ ID NO: 3, and a light chain complementary determining region comprising SEQ ID NO: 4, SEQ ID NO: 5 and/or SEQ ID NO: 8; d) a heavy chain complementary determining region comprising SEQ ID NO: 1, SEQ ID NO: 7 and/or SEQ ID NO: 3, and a light chain complementary determining region comprising SEQ ID NO: 4, SEQ ID NO: 5 and/or SEQ ID NO: 8; or e) a heavy chain complementary determining region comprising SEQ ID NO: 9, SEQ ID NO: 10 and/or SEQ ID NO: 11, and a light chain complementary determining region comprising SEQ ID NO: 12, SEQ ID NO: 13 and/or SEQ ID NO: 14.

As used herein, "MT01-L1" refers to a human-mouse chimeric monoclonal antibody having a heavy chain variable region shown in SEQ ID NO: 15, a light chain variable region shown in SEQ ID NO: 16, and a human-derived IgG1/κ isotype constant region.

As used herein, "MT01-L1(M1)" refers to a human-mouse chimeric monoclonal antibody having a heavy chain variable region shown in SEQ ID NO: 17, a light chain variable region shown in SEQ ID NO: 16, and a human-derived IgG1/κ isotype constant region.

As used herein, "MT01-L1(M2)" refers to a human-mouse chimeric monoclonal antibody having a heavy chain variable region shown in SEQ ID NO: 15, a light chain variable region shown in SEQ ID NO: 18, and a human-derived IgG1/κ isotype constant region.

As used herein, "MT01-L1(M1/M2)" refers to a human-mouse chimeric monoclonal antibody having a heavy chain variable region shown in SEQ ID NO: 17, a light chain variable region shown in SEQ ID NO: 18, and a human-derived IgG1/κ isotype constant region.

As used herein, "MT01-L1(G2)" refers to a human-mouse chimeric monoclonal antibody having a heavy chain variable region shown in SEQ ID NO:

15, a light chain variable region shown in SEQ ID NO: 16, and a human-derived IgG2/κ isotype constant region.

As used herein, "MT01-L2" refers to a human-mouse chimeric monoclonal antibody having a heavy chain variable region shown in SEQ ID NO: 19, a light chain variable region shown in SEQ ID NO: 20, and a human-derived IgG1/κ isotype constant region.

As used herein, "MT01-L2(G2)" refers to a human-mouse chimeric antibody monoclonal antibody having a heavy chain variable region shown in SEQ ID NO: 19, a light chain variable region shown in SEQ ID NO: 20, and a human-derived IgG2/κ isotype constant region.

As used herein, "MT01-C1" refers to a humanized monoclonal antibody having a heavy chain variable region shown in SEQ ID NO: 29, a light chain variable region shown in SEQ ID NO: 30, and a human-derived IgG1/κ isotype constant region.

As used herein, "MT01-C1(G2)" refers to a humanized monoclonal antibody having a heavy chain variable region shown in SEQ ID NO: 29, a light chain variable region shown in SEQ ID NO: 30, and a human-derived IgG2/κ isotype constant region.

Those skilled in the art will understand that the CDR sequences provided herein can be modified to contain one or more substitutions of amino acid, thereby resulting in improved biological activities, such as an increased binding affinity to human OX40. For example, a library of antibody variants (such as Fab or scFv variants) can be generated and expressed with phage display technology, and then screened for the antibodies with binding affinity to human OX40. In another example, computer software can be used to simulate the binding of the antibodies to human OX40, and identify the amino acid residues on the antibodies that form the binding interface. The substitution of these residues may be avoided so as to prevent reduction in binding affinity, or these residues can be targeted for substitution to form a stronger binding. In certain embodiments, at least one (or all) of the substitutions in the CDR sequences is (are) conservative substitution(s).

In certain embodiments, the antibodies or antigen binding fragments thereof comprise one or more CDR sequences having at least 80% (e.g. at least 85%, 88%, 90%, 91%, 92%, 93%, 94%, 95%, 96%, 97%, 98%, 99%) sequence identity to those provided in Table 1, and at the same time retain their binding affinities to human OX40 at a level similar to or even higher than their parental antibodies having substantially the same sequences except that the corresponding CDR sequences have 100% sequence identity to those provided in Table 1.

In some embodiments, the anti-OX40 antibodies or antigen binding fragments thereof described herein are capable of specifically binding to human OX40 with a binding affinity (Kd) of ≤$10^{-7}$ M, as measured by the surface plasmon resonance method. The binding affinity can be represented by a $K_D$ value, which is calculated as the ratio of dissociation rate to association rate ($k_{off}/k_{on}$) when the binding between the antigen and the antigen-binding molecule reaches an equilibrium. The antigen-binding affinity (e.g. $K_D$) can be appropriately determined using suitable methods known in the art, including, for example, plasmon resonance binding assay using an instrument from such as Biacore.

In certain embodiments, the antibodies or antigen binding fragments thereof described herein bind to human OX40 with an EC50 (i.e., half-binding concentration) of 10 ng/mL- 10 μg/mL. The binding of the antibodies to human OX40 can be measured by methods known in the art, such as sandwich methods, such as ELISA, Western blot, FACS, or other binding assays. In an illustrative example, the antibody to be tested (i.e. the primary antibody) is allowed to bind to immobilized human OX40 or cells expressing human OX40, then the unbound antibody is washed away, and a labeled secondary antibody is introduced which can bind to the primary antibody, thus allowing the detection of the bound secondary antibody. The detection can be conducted with a microplate reader and a microplate when immobilized OX40 is used, or by FACS assay when cells expressing human OX40 are used.

In certain embodiments, the antibodies or antigen binding fragments thereof described herein bind to human OX40 with an EC50 (i.e., 50% effective concentration) of 0.1 μg/mL to 10 μg/mL (measured by FACS assay).

In certain embodiments, the antibodies or antigen binding fragments thereof described herein can activate human OX40 signaling pathway, and thus provide biological activities including, for example, induction of activated T cells to produce cytokines (such as CD4+ T cells and CD8+ T cells), induction of proliferation of activated T cells (such as CD4+ T cells and CD8+ T cells), and reversal of the inhibitory function of regulatory Treg.

The anti-OX40 antibodies or antigen binding fragments thereof are specific to human OX40. In certain embodiments, the antibodies or antigen binding fragments thereof do not bind to mouse OX40, but bind to monkey OX40 with a binding affinity similar to that of human OX40. For example, the binding of exemplary antibodies MT01-L1 and MT01-L2 to mouse OX40 could not be detected by common binding assays such as FACS assay, while FACS detected that these antibodies bind to monkey OX40 with an affinity or EC50 value similar to that of human OX40.

In some embodiments, the anti-OX40 antibodies or antigen binding fragments thereof have a constant region of IgG2 isotype, which have reduced or eliminated effector functions. Effector functions such as ADCC and CDC can lead to cytotoxicity to OX40 expressing cells. Some normal cells can express OX40. In order to avoid potential undesired toxicity to these normal cells, the certain embodiments of the antibodies or antigen binding fragments thereof described herein have reduced or even eliminated effector functions. It is known that many assays are used to estimate ADCC or CDC activity, such as Fc receptor binding assay, complement C1q binding assay, and cell lysis method, which can be easily selected by those skilled in the art. Without wishing to be bound by theories, it is believed that the antibodies with reduced or eliminated effector functions such as ADCC and CDC will have no or minimized cytotoxicity to OX40-expressing cells (such as those normal cells), thus avoiding undesirable side effects.

In some embodiments, the anti-OX40 antibodies or antigen binding fragments thereof described herein have reduced side effects. For example, the anti-OX40 antibody or antigen binding fragment thereof may have a fully human IgG sequence, so its immunogenicity is lower than those of humanized antibodies. In another example, the anti-OX40 antibody or antigen binding fragment thereof may have the form of IgG2 or IgG4 to eliminate ADCC and CDC.

In some embodiments, the advantage of the anti-OX40 antibodies and antigen binding fragments thereof described herein is that they can be used in combination with immunogenic agents, such as tumor cells, purified tumor antigens, cells transfected with genes encoding immune stimulating factors, and tumor vaccines. In addition, the anti-OX40 antibodies or antigen binding fragments thereof can be included in combination therapies, comprising standard chemotherapies and radiotherapies, target-based small molecule therapies, other emerging immune checkpoint modulator therapies. In some embodiments, the antibodies or antigen binding fragments thereof can be used as the base molecules for antibody-drug conjugates, bispecific or multivalent antibodies.

The anti-OX40 antibodies or antigen binding fragments thereof described herein can be monoclonal antibodies, polyclonal antibodies, fully human antibodies, humanized antibodies, chimeric antibodies, recombinant antibodies, bispecific antibodies, labeled antibodies, bivalent antibodies, or anti-idiotypic antibodies. A recombinant antibody is an antibody prepared in vitro using a recombinant method rather than in an animal. A bispecific or bivalent antibody is an artificial antibody having the fragments of two different monoclonal antibodies, which can bind to two different antigens. An antibody or antigen binding fragment thereof that is "bivalent" comprises two antigen-binding sites. The two antigen binding sites may bind to the same antigen, or they may each bind to a different antigen, in which case the antibody or antigen binding fragment is characterized as "bispecific".

In some embodiments, the anti-OX40 antibodies or antigen binding fragments thereof described herein are fully human antibodies. In some embodiments, the fully human antibodies are prepared using recombinant methods. For example, a transgenic animal such as a mouse can be prepared to carry a transgene or a transchromosome of human immunoglobulin gene, and thus can produce a fully human antibody after immunization with a suitable antigen such as human OX40. The fully human antibodies can be isolated from such a transgenic animal, or alternatively, they can be prepared by hybridoma technology, in which the spleen cells of the transgenic animal are fused with immortalized cell lines to produce hybridoma cells secreting the fully human antibodies.

In some embodiments, the anti-OX40 antibodies or antigen binding fragments thereof described herein are a camelized single domain antibody, a diabody, a scFv, an scFv dimer, a BsFv, a dsFv, a (dsFv)2, a dsFv-dsFv', an Fv fragment, an Fab, an Fab', an F(ab')2, a ds diabody, a nanobody, a domain antibody, or a bivalent domain antibody.

In some embodiments, the anti-OX40 antibodies or antigen binding fragments thereof provided herein further comprise an immunoglobulin constant region. In some embodiments, the immunoglobulin constant regions comprise a heavy chain and/or a light chain constant region. The heavy chain constant region comprises CH1, CH1-CH2, or CH1-CH3 region. In some embodiments, the immunoglobulin constant regions may further comprise one or more modifications to confer desirable properties. For example, the constant region may be modified to reduce or eliminate one or more effector functions, thereby improving binding to FcRn receptor, or to introduce one or more cysteine residues.

In certain embodiments, the anti-OX40 antibodies or antigen binding fragments thereof further comprise a conjugate. It is contemplated that the antibodies or antigen binding fragments provided herein may be linked to a variety of conjugates (see, for example, "Conjugate Vaccines", Contributions to Microbiology and Immunology, J. M. Cruse and R. E. Lewis, Jr. (eds.), Carger Press, New York, (1989)). These conjugates may be linked to the antibodies or antigen binding fragments by covalent binding, affinity binding, intercalation, coordinate binding, complexation, association, blending, or addition, among other methods. In certain embodiments, the antibodies or antigen binding fragments disclosed herein may be engineered to contain specific sites other than the epitope binding moiety that may be utilized for binding to one or more conjugates. For example, such a site may comprise one or more reactive amino acid residues, such as cysteine or histidine residues, to facilitate covalent linkage to a conjugate. In certain embodiments, the antibodies may be linked to a conjugate indirectly, or through another conjugate. For example, the antibody or antigen binding fragment may be conjugated to biotin, then indirectly conjugated to a second conjugate that is conjugated to avidin. The conjugate can be a detectable label, a pharmacokinetic modification moiety, a purification moiety, or a cytotoxic moiety. Examples of detectable labels may include fluorescent labels (e.g. fluorescein, rhodamine, dansyl, phycoerythrin, or Texas Red), enzyme-substrate labels (e.g. horseradish peroxidase, alkaline phosphatase, luceriferase, glucoamylase, lysozyme, saccharide oxidase or β-D-galactosidase), stable isotopes or radioisotopes, chromophoric moieties, digoxigenin, biotin/avidin, DNA molecules or gold for detection. In certain embodiments, the conjugates can be pharmacokinetic modification moieties such as PEG which help extend the half-life of the antibody. Other suitable polymers comprise, such as, carboxymethylcellulose, dextran, polyvinyl alcohol, polyvinyl pyrrolidone, ethylene glycol/propylene glycol copolymers, and the like. In certain embodiments, the conjugates can be purification moieties such as magnetic beads. A "cytotoxic" moiety can be any agent that is detrimental to cells or that can damage or kill cells. Examples of cytotoxic moiety include, without limitation, taxol, cytochalasin B, gramicidin D, ethidium bromide, emetine, mitomycin, etoposide, teniposide, vincristine, vinblastine, colchicin, doxorubicin, daunorubicin, dihydroxyanthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil, dacarbazine), alkylating agents (e.g., nitrogen mustard, thiotepa, chlorambucil, melphalan, carmustine (BSNU) and lomustine (CCNU), cyclophosphamide, busulfan, dibromomannitol, streptozotocin, mitomycin C, and cis-dichlorodiamineplatinum (II) (DDP), cisplatin, anthracyclines (e.g., daunorubicin (formerly known as daunomycin) and doxorubicin), antibiotics (e.g., dactinomycin (formerly known as actinomycin), bleomycin, mithramycin, and anthramycin (AMC)), and anti-mitotic agents (e.g., vincristine and vinblastine).

Polynucleotides and Recombinant Methods

Using genetic engineering techniques known in the art, the amino acid sequences in Table 1 can be converted into the corresponding DNA encoding sequences. Due to the degeneracy of genetic codon, the converted DNA sequences may not be completely identical, while the encoded protein sequences remain unchanged.

The vectors which comprise polynucleotides encoding the anti-OX40 antibodies or antigen binding fragments thereof (e.g. comprising the sequences shown in Table 1) can be introduced into host cells for cloning (amplifying the DNAs) or for gene expression, using recombinant techniques known in the art. In another embodiment, the antibody may be produced by a homologous recombination known in the art. The DNAs encoding the monoclonal antibody can be isolated and sequenced using conventional procedures (e.g., using oligonucleotide probes that can specifically bind to genes encoding the heavy and light chains of the antibody). Various vectors are available. The vector components generally include, but are not limited to, two or more of the following: a signal sequence, an origin of replication, one or more marker genes, an enhancer sequence, a promoter (e.g. SV40, CMV, EF-1α), and a transcription terminator sequence.

In some embodiments, the vector systems include mammalian, bacterial, or yeast systems, etc., and include plasmids such as, but not limited to, pALTER, pBAD, pcDNA, pCal, pL, pELpGEMEX, pGEX, pCLpCMV, pEGFP, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS420, pLexA, pACT2, etc., and other vectors available from laboratories or commercially. Suitable vectors may include plasmid or viral vectors (e.g., replication defective retroviruses, adenoviruses and adeno-associated viruses).

The vectors which comprise the polynucleotide sequences encoding the antibodies or antigen binding fragments can be introduced into host cells for cloning or gene expression. Suitable host cells for cloning or expressing the DNAs in the vectors in the present disclosure are prokaryotic cells, yeasts or higher eukaryotic cells described above. Suitable prokaryotic cells for use in the present disclosure include eubacteria such as Gram-negative bacteria or Gram-positive bacteria, for example, Enterobacteriaceae such as *E. coli, Enterobacter, Erwinia, Klebsiella, Proteus, Salmonella* e.g., *Salmonella typhimurium, Serratia* e.g., *Serratia marcescans,* and *Shigella,* as well as Bacilli such as *B. subtilis* and *B. licheniformis, Pseudomonas* such as *P. aeruginosa,* and *Streptomyces.*

In addition to prokaryotic cells, eukaryotic microorganisms such as filamentous fungi or yeasts can also be used as host cells to clone or express vectors encoding the anti-OX40 antibodies. *Saccharomyces cerevisiae,* or baker's yeast, is the most commonly used lower eukaryotic host microorganism. However, a number of other genera, species, and strains are commonly available and applicable in the present disclosure, such as *Schizosaccharomyces pombe; Kluyveromyces* hosts such as, *K. lactis, K. fragilis* (ATCC 12,424), *K. bulgaricus* (ATCC 16,045), *K. wickerhamii* (ATCC 24,178), *K. waltii* (ATCC 56,500), *K. drosophilarum* (ATCC 36,906), *K. thermotolerans,* and *K. marxianus; Yarrowia lipolytica* (EP 402,226); *Pichia pastoris* (EP 183, 070); *Candida; Trichoderma reesia* (EP 244,234); *Neurospora crassa; Schwanniomyces* such as *Schwanniomyces occidentalis;* and filamentous fungi such as *Neurospora, Penicillium, Tolypocladium,* and *Aspergillus* such as *A. nidulans* and *A. niger.*

Suitable host cells for the expression of glycosylated antibodies or antigen-fragments provided herein are derived from multicellular organisms. Examples of invertebrate cells include plant and insect cells. Numerous baculoviral strains and their variants and corresponding permissive insect host cells have been found from hosts such as *Spodoptera frugiperda* (caterpillar), *Aedes aegypti* (mosquito), *Aedes albopictus* (mosquito), *Drosophila melanogaster* (fruit fly), and *Bombyx mori.* A variety of viral strains for transfection are publicly available, e.g., the Bm-5 variants of *Autographa californica* NPV and *Bombyx mori* NPV, which can be used in the present disclosure, particularly for transfection of *Spodoptera frugiperda* cells. Plant cell cultures of cotton, corn, potato, soybean, *petunia,* tomato, and tobacco can also be utilized as hosts.

However, vertebrate cells have drawn the greatest interest, and the cultivation of vertebrate cells (tissue culture) has become a routine procedure. Examples of useful mammalian host cells are SV40-transformed monkey kidney CV1 line (COS-7, ATCC CRL 1651); human embryonic kidney line (293 or 293 cell subclones cultured in suspension, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77: 4216 (1980)); mouse testicular sertoli cells (TM4, Mather, Biol. Reprod. 23: 243-251(1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383: 44-68(1982)); MRC 5 cells; FS4 cells; and human hepatocellular carcinoma cell line (HepG2). In certain preferred embodiments, the host cells are 293F cells.

Host cells are transformed with the above-described expression or cloning vectors that can produce the anti-OX40 antibodies and cultured in conventional nutrient media modified as appropriate for inducing promoters, selecting transformed cells, or amplifying genes encoding the target sequences.

The host cells used to produce the antibodies or antigen binding fragments thereof in the present disclosure may be cultured in a variety of media known in the art. The media may also contain any other necessary additives at appropriate concentrations known in the art. The culture conditions, such as temperature, pH, and the like, are those previously used for selection of the host cells for expression, and are apparent to the ordinarily skilled artisan.

When recombinant techniques are used, the antibodies can be produced intracellularly, in the periplasmic space, or directly secreted into the media. If the antibodies are produced intracellularly, the particulate debris of either host cells or lysed fragments is first removed, for example, by centrifugation or sonication process. Carter et al., Bio/Technology 10: 163-167(1992) describes a procedure for isolating antibodies which are secreted into the periplasmic space of *E. coli.* Briefly, cell paste is thawed in the presence of uranyl acetate (pH 3.5), EDTA, and phenylmethylsulfonyl fluoride (PMSF) over about 30 min. Cell debris can be removed by centrifugation. If the antibodies are secreted into the media, the supernatants from such expression systems are generally first concentrated using a commercially available protein concentration filter, for example, an Amicon or Millipore Pellicon ultrafiltration unit. Protease inhibitors such as PMSF may be added in any of the foregoing steps to inhibit proteolysis, and antibiotics may be added to prevent the growth of adventitious contaminants.

Antibodies prepared from the cells can be purified using purification methods, such as hydroxylapatite chromatography, gel electrophoresis, dialysis, DEAE-cellulose ion exchange chromatography, ammonium sulfate precipitation, salting out, and affinity chromatography, with affinity chromatography being the preferred purification technique. Whether protein A is suitable as an affinity ligand depends on the types of the antibodies and any immunoglobulin Fc domains that are present in the antibodies. Protein A can be used to purify the antibodies that are based on human γ1, γ2, or γ4 heavy chains (Lindmark et al., J. Immunol. Meth. 62: 1-13(1983)). Protein G is suitable for all mouse isotypes and for human γ3 (Guss et al., EMBO J. 5:1567-1575(1986)). Agarose is the most commonly used affinity ligand attachment matrix, but other matrices can also be used. Mechanically stable matrices such as controlled pore glass or poly (styrene)benzene can achieve a faster flow rate and a shorter processing time than those can be achieved with agarose. If the antibody comprises a CH3 domain, the Bakerbond ABX™ resin (J. T. Baker, Phillipsburg, N.J.) can be used for purification. Other techniques for protein purification such as fractionation on an ion-exchange column, ethanol precipitation, reverse phase HPLC, silica gel chromatography, heparin sepharose chromatography based on an anion or cation exchange resin (such as a polyaspartic acid column), chromatofocusing, SDS-PAGE, and ammonium sulfate precipitation are also determined depending on the antibody to be obtained.

After any preliminary purification step(s), the mixture comprising the antibody of interest and impurities may be subjected to low pH hydrophobic interaction chromatography using an elution buffer at a pH of about 2.5-4.5, which is preferably performed at low salt concentrations (e.g., salt concentration of about 0-0.25M).

Kits

The present disclosure provides kits comprising the anti-OX40 antibodies or the antigen binding fragments thereof. In some embodiments, the kits are useful for detecting the presence or the level of OX40 in biological samples. The biological samples may include cells or a tissue.

In some embodiments, the kits comprise the anti-OX40 antibodies or antigen binding fragments thereof conjugated with a detectable label. In some embodiments, the kits comprise the unlabeled anti-OX40 antibodies or antigen binding fragments thereof, and further comprise secondary labeled antibodies which are capable of binding to the unlabeled anti-OX40 antibodies or antigen binding fragments thereof. The kits may further comprise an instruction for use, and a package that separates each component in the kits.

In some embodiments, the anti-OX40 antibodies or antigen binding fragments thereof are associated with substrates or instruments for sandwich assays such as ELISA, or immunographic assay. Suitable substrates or instruments can be, for example, a microwell plate and a test strip.

Pharmaceutical Compositions and Treatment Methods

The present disclosure further provides pharmaceutical compositions comprising the anti-OX40 antibody or antigen binding fragment thereof, and one or more pharmaceutically acceptable carriers.

The pharmaceutical acceptable carriers for use in the pharmaceutical compositions disclosed herein may include, for example, pharmaceutically acceptable liquids, gels, or solid carriers, aqueous vehicles, non-aqueous vehicles, antimicrobial agents, isotonic agents, buffers, antioxidants, anesthetics, suspending/dispending agents, chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated methylxanisole, butylated hydroxytoluene, and/or propyl gallate. As disclosed herein, inclusion of one or more antioxidants such as methionine in a composition comprising the antibody or antigen binding fragment thereof as disclosed herein will reduce oxidation of the antibody or antigen binding fragment thereof. This reduction in oxidation can prevent or reduce loss of binding affinity, thereby improving the antibody stability and extending shelf-life. Therefore, in certain embodiments, the compositions provided by the present disclosure comprise one or more antibodies or antigen binding fragments thereof and one or more antioxidants such as methionine. Further provided are various methods for preventing oxidation of, extending the shelf-life of, and/or improving the activity of the antibodies or antigen binding fragments thereof by mixing the antibodies or antigen binding fragments thereof with one or more antioxidants such as methionine.

Further, the pharmaceutical acceptable carriers may comprise, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), chelating agents such as EDTA (ethylenediaminetetraacetic acid) or EGTA (ethylene glycol-bis(2-aminoethyl ether)-tetraacetic acid), ethyl alcohol, polyethylene glycol, propylene glycol, sodium hydroxide, hydrochloric acid, citric acid, or lactic acid. Antimicrobial agents as carriers may be added to pharmaceutical compositions in multiple-dose containers, which include phenols or cresols, mercurials, benzyl alcohol, chlorobutanol, methyl and propyl parabens, thimerosal, benzalkonium chloride and benzethonium chloride. Suitable excipients may include, for example, water, saline, dextrose, glycerol, or ethanol. Suitable non-toxic auxiliary substances may include, for example, emulsifying agents, pH buffering agents, stabilizers, solubilizers, or agents such as sodium acetate, sorbitan laurate, triethanolamine oleate, or cyclodextrin.

The pharmaceutical compositions can be liquid solutions, suspensions, emulsions, pills, capsules, tablets, sustained release formulations, or powders. Oral formulations can comprise standard carriers such as pharmaceutical grade mannitol, lactose, starch, magnesium stearate, polyvinyl pyrollidone, sodium saccharine, cellulose, magnesium carbonate, etc.

In certain embodiments, the pharmaceutical compositions are formulated into injectable compositions. The injectable pharmaceutical compositions may be prepared in any conventional forms, such as liquid solution, suspension, emulsion, or solid forms suitable for generating liquid solution, suspension, or emulsion. Injection preparations may comprise sterile and/or pyrogen-free solutions ready for use, sterile dry soluble substances ready to be combined with a solvent just prior to use, such as lyophilized powders, including hypodermic tablets, sterile suspensions ready for injection, sterile dry insoluble products ready to be combined with a vehicle just prior to use, and sterile and/or pyrogen-free emulsions. The solutions may be either aqueous or non-aqueous.

In certain embodiments, injection preparations in a unit dosage form are packaged in an ampoule, a vial or a syringe with a needle. It is known in the art that all preparations for injection administration should be sterile and pyrogen-free.

In certain embodiments, sterile, lyophilized powders can be prepared by dissolving the antibodies or antigen binding fragments thereof as disclosed herein in a suitable solvent. The solvent may contain another pharmacological component that can increase the stability of the powder or the reconstituted solution prepared from the powder, or improve the powder or the reconstituted solution. Suitable excipients include, but are not limited to, water, dextrose, sorbital, fructose, corn syrup, xylitol, glycerin, glucose, sucrose or other suitable agent. The solvent may contain a buffer, such as citrate buffer, sodium or potassium phosphate buffer or other such buffer known to those skilled in the art. In one embodiment, the pH of the buffer is neutral. A subsequent sterile filtration of the solution followed by lyophilization under standard conditions known to those skilled in the art provides a desirable formulation. In one embodiment, the resulting solution is dispensed into vials for lyophilization. Each vial can contain a single dosage or multiple dosages of the anti-OX40 antibody or antigen binding fragment thereof or composition thereof. The filling volume of each vial can be slightly higher than that needed for each dosage or multiple dosages (e.g., 10% overdose), so as to ensure accurate sample withdrawal and accurate dosing. The lyophilized powders can be stored under appropriate conditions, such as at about 4° C. to room temperature.

Reconstitution of a lyophilized powder with water for injection provides a formulation for injection. In one embodiment, the lyophilized powder is added into sterile and pyrogen-free water or other suitable liquid carrier for reconstitution. The precise amount can be determined by the selected therapy, and can be determined empirically.

There is also provided a treatment method, comprising administering to a subject in need thereof a therapeutically effective amount of the anti-OX40 antibody or antigen binding fragment thereof as described herein, thereby treating or preventing a condition or a disorder associated with OX40. In another aspect, there is also provided a method for treating a condition in a subject that would benefit from an upregulated immune response, comprising administering a therapeutically effective amount of the anti-OX40 antibody or antigen binding fragment thereof as described herein to the subject in need thereof.

The therapeutically effective amounts of the antibodies or antigen binding fragments thereof as provided herein will depend on various factors known in the art, such as body weight, age, past medical history, current treatment, health status of the subject and potential for cross infection, allergy, hypersensitivity and side effects, as well as administration route and the degree of tumor progression. Those skilled in the art (e.g., doctors or veterinarians) can reduce or increase the dosage in proportion according to these or other conditions or requirements.

In certain embodiments, the anti-OX40 antibodies or antigen binding fragments thereof as provided herein may be administered at a therapeutically effective dosage of between about 0.01 mg/kg and about 100 mg/kg. In certain embodiments, the anti-OX40 antibodies or antigen binding fragments thereof are administered at a dosage of about 50 mg/kg or less, and in certain embodiments, the dosages are 10 mg/kg or less, 5 mg/kg or less, 1 mg/kg or less, 0.5 mg/kg or less, or 0.1 mg/kg or less. A specific dose can be administered at multiple intervals, such as once a day, twice a day or more, twice a month or more, once a week, once every two weeks, once every three weeks, once a month, once every two months or once every more months. In certain embodiments, the administration dosages may change over the course of treatment. For example, in certain embodiments the initial administration dosages may be higher than the subsequent administration dosages. In certain embodiments, the administration dosages may be adjusted over the course of treatment depending on the responses of subjects.

Dosage regimens may be adjusted to provide the optimal response (e.g., a therapeutic response). For example, the administration is conducted as a single dose or multiple divided doses over two periods of time.

The antibodies or antigen binding fragments disclosed herein may be administered by any routes known in the art, such as administered by injection (e.g., subcutaneous injection, intraperitoneal injection, intravenous injection comprising intravenous infusion, intramuscular injection, or intradermal injection) or administered by non-injection routes (e.g., oral, intranasal, sublingual, rectal, or topical administration).

Conditions and disorders associated with OX40 can be immune-related diseases or disorders. In certain embodiments, the conditions and disorders associated with OX40 include tumors and cancers, for example non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphoma, myeloma, mycoses fungoids, Merkel cell cancer and other hematological malignancies, such as classical Hodgkin's lymphoma (CHL), primary mediastinal large B-cell lymphoma, T-cell/histiocyte-rich B-cell lymphoma, EBV-positive and -negative PTLD, and EBV-associated diffuse large B-cell lymphoma (DLBCL), plasmablastic lymphoma, extranodal NK/T-cell lymphoma, nasopharyngeal carcinoma, and HHV8-associated primary effusion lymphoma, Hodgkin's lymphoma, neoplasm of the central nervous system (CNS), such as primary CNS lymphoma, spinal axis tumor, brain stem glioma. In certain embodiments, the tumors and cancers are metastatic, especially the metastatic tumors expressing OX40. In certain embodiments, the OX40 associated conditions and disorders comprise chronic viral infection, for example, viral infection of hepatitis B (HBV), hepatitis C (HCV), herpes virus, Epstein-Barr virus, HIV, cytomegalovirus, herpes simplex virus type I, herpes simplex virus type II, human papilloma virus, adenovirus, Kaposi sarcoma associated herpes virus epidemics, Torquetenovirus, JC virus or BK virus.

Methods of Use

The present disclosure further provides methods of using the anti-OX40 antibodies or antigen binding fragments thereof.

In some embodiments, the present disclosure provides methods of treating an OX40 associated condition or disorder in a subject, comprising administering a therapeutically effective amount of the antibody or antigen binding fragment thereof described herein. In some embodiments, the subjects have been identified as having a disorder or a condition likely to respond to an OX40 agonist.

The presence and level of OX40 in a target biological tissue can indicate whether the individual from whom the biological sample is derived may respond to an OX40 agonist. Various methods can be used to determine the presence or level of OX40 in a biological sample to be tested from the individual. For example, the biological sample to be tested can be exposed to the anti-OX40 antibody or antigen binding fragment thereof, which binds to and detects the expressed OX40 protein. In some embodiments, the samples to be tested are derived from cancer cells or tissues, or immune cells that enter a tumor. In some embodiments, the presence or up-regulated level of OX40 in the biological sample to be tested indicates the likelihood of response. The term "up-regulated" as used herein refers to an overall increase of no less than 10%, 15%, 20%, 25%, 30%, 35%, 40%, 45%, 50%, 55%, 60%, 65%, 70%, 75%, 80% or greater, in the OX40 protein level in a sample to be detected using the antibody or antigen binding fragment thereof described herein, as compared to the OX40 protein level in a reference sample measured using the same antibody. The reference sample can be a control sample obtained from a healthy or disease-free individual, or a healthy or disease-free sample obtained from the same individual from whom the sample to be tested is obtained. For example, the reference sample can be a disease-free sample adjacent to or in the neighborhood of the sample to be tested (e.g. tumor).

The antibodies or antigen binding fragments disclosed herein may be administered alone or in combination with one or more additional therapies or agents. For example, the antibodies or antigen binding fragments disclosed herein may be administered in combination with chemotherapy, radiation therapy, surgery for the treatment of cancer (e.g., tumorectomy), one or more anti-emetics or other treatments for complications arising from chemotherapy, or any other therapeutic agent for cancer or any therapeutic agent for the disorder mediated by OX40. In certain such embodiments, the antibodies or antigen binding fragments as disclosed herein, when administered in combination with one or more therapeutic agents, may be administered simultaneously with the one or more therapeutic agents, and in certain such embodiments, the antibodies and antigen binding fragments may be administered as a part of the same pharmaceutical composition. However, the antibodies or antigen binding fragments administered "in combination" with another therapeutic agent does not have to be administered simultaneously with the therapeutic agent or administered in the same composition with the therapeutic agent. The term "in combination" as used in the present disclosure also means that the antibody or antigen binding fragment administered prior to or after another therapeutic agent is also considered to be administered "in combination" with that therapeutic agent, even if the antibody or antigen binding fragment thereof and the second agent are administered via different routes. Where possible, additional therapeutic agents administered in combination with the antibodies or antigen binding fragments thereof disclosed herein are administered according to the schedule listed in the instructions for the additional therapeutic agents, or according to the Physicians' Desk Reference 2003 (Physicians' Desk Reference, 57th Ed; Medical Economics Company; ISBN: 1563634457; 57th edition (November 2002)) or according to protocols well known in the art.

In certain embodiments, the therapeutic agents can induce or boost immune response against cancer. For example, a tumor vaccine can be used to induce immune response to a certain tumor or cancer. Cytokine therapies can be used to enhance the presentation of tumor antigens to the immune system. Examples of cytokine therapy include, without limitation, interferons such as interferon-α, β, and γ, colony stimulating factors such as macrophage CSF, granulocyte macrophage CSF, and granulocyte CSF, interleukins such IL-1, IL-la, IL-2, IL-3, IL-4, IL-5, IL-6, IL-7, IL-8, IL-9, IL-10, IL-11, and IL-12, tumor necrosis factors such as TNF-α and TNF-β. Agents that inactivate immunosuppressive targets can also be used, such as PD-L1/PD-1 antibody, TGF-β inhibitor, IL-10 inhibitor and Fas ligand inhibitor. Another group of agents include those that activate immune response to tumor or cancer cells, for example, those that enhance T cell activation (e.g. agonists of T cell costimulatory molecules such as CTLA-4, ICOS), and those that enhance dendritic cell function and antigen presentation.

The present disclosure further provides methods for monitoring treatment response or disease progression in a subject treated with an OX40 agonist, comprising determining the presence or level of OX40 in a biological sample to be tested from the subject using the anti-OX40 antibody or antigen binding fragment thereof described herein. In certain embodiments, the methods further comprise comparing the OX40 level in the biological sample to be tested with the OX40 level in a comparable sample previously obtained from the same subject, wherein reducing or slowing or ceasing of increase in the OX40 level in the biological sample to be tested indicates a positive treatment response or controlled disease progression. The comparable sample may be of the same type as the sample to be tested, but it is obtained from the same individual before treatment or at an early stage of treatment.

The following examples are intended to better illustrate the invention and are not to be construed as limiting the scope of the invention. All specific compositions, materials, and methods described below, in whole or in part, are within the scope of the present disclosure. These specific compositions, materials, and methods are not intended to limit the invention, but merely to illustrate specific embodiments within the scope of the invention. Those skilled in the art may develop equivalent compositions, materials, and methods without adding inventive step and without departing from the scope of the invention. It will be understood that various modifications made to the methods of the present disclosure may still be included in the scope of the invention. The inventors intend to include such changes within the scope of the present disclosure.

Example 1: Acquisition of Anti-Human OX40 Activating Monoclonal Antibodies

A CHO cell line overexpressing OX40 was constructed by the inventors of the present disclosure, which was used to immunize mice and perform hybridoma cell fusion. Through the antigen-antibody binding assay and cell function screening, a series of mouse-derived antibodies with stronger ELISA binding activity and OX40 activation function were obtained. The sequences of the variable regions VH and VL of each antibody were obtained by sequencing, and the human-mouse chimeric antibodies were designed and expressed accordingly, wherein the heavy chain complementary determining region is selected from one or more of the following sequences: SEQ ID NO: 1, SEQ ID NO: 2, SEQ ID NO: 3, SEQ ID NO: 7, SEQ ID NO: 9, SEQ ID NO: 10, and SEQ ID NO: 11, and the light chain complementary determining region is selected from one or more of the following sequences: SEQ ID NO: 4, SEQ ID NO: 5, SEQ ID NO: 6, SEQ ID NO: 8, SEQ ID NO: 12, SEQ ID NO: 13, and SEQ ID NO: 14.

More preferably, the heavy chain complementary determining region is SEQ ID NO: 1, SEQ ID NO: 2 and/or SEQ ID NO: 3; SEQ ID NO: 1, SEQ ID NO: 7 and/or SEQ ID NO: 3; or SEQ ID NO: 9, SEQ ID NO: 10 and/or SEQ ID NO: 11. The light chain complementary determining region is SEQ ID NO: 4, SEQ ID NO: 5 and/or SEQ ID NO: 6; SEQ ID NO: 4, SEQ ID NO: 5 and/or SEQ ID NO: 8; or SEQ ID NO: 12, SEQ ID NO: 13 and/or SEQ ID NO: 14.

In the preferred examples of the invention, the heavy chain complementary determining regions and the light chain complementary determining regions are shown in Table 1, respectively.

a. The heavy chain complementary determining region comprises SEQ ID NO: 1, SEQ ID NO: 2 and SEQ ID NO:

3, and the light chain complementary determining region comprises SEQ ID NO: 4, SEQ ID NO: 5 and SEQ ID NO: 6;

b. The heavy chain complementary determining region comprises SEQ ID NO: 1, SEQ ID NO: 7 and SEQ ID NO: 3, and the light chain complementary determining region comprises SEQ ID NO: 4, SEQ ID NO: 5 and SEQ ID NO: 6;

c. The heavy chain complementary determining region comprises SEQ ID NO: 1, SEQ ID NO: 2 and SEQ ID NO: 3, and the light chain complementary determining region comprises SEQ ID NO: 4, SEQ ID NO: 5 and SEQ ID NO: 8;

d. The heavy chain complementary determining region comprises SEQ ID NO: 1, SEQ ID NO: 7 and SEQ ID NO: 3, and the light chain complementary determining region comprises SEQ ID NO: 4, SEQ ID NO: 5 and SEQ ID NO: 8; or e. The heavy chain complementary determining region comprises SEQ ID NO: 9, SEQ ID NO: 10 and SEQ ID NO: 11, and the light chain complementary determining region comprises SEQ ID NO: 12, SEQ ID NO: 13 and SEQ ID NO: 14.

Specifically, in Example 1, a CHO cell line overexpressing OX40 was constructed by the inventors, which was used to immunize the mice and perform hybridoma cell fusion with SP2/0-AG14 cell line. Through the antigen-antibody binding assay and cell function screening, a series of mouse antibodies with stronger ELISA binding activity and OX40 activation function were obtained. The sequences of the variable regions VH and VL of each antibody were obtained by sequencing, and the human-mouse chimeric antibodies were designed and expressed accordingly, including MT01-L1 and MT01-L2.

In order to enhance the antibody stability and reduce the influence of possible oxidation and isomerization on the purity and activity of the antibodies, mutation was made at a specific site with potential instability in the heavy and light chain V regions of the antibodies. For example, amino acid 57 in the heavy chain of MT01-L1 was mutated from glycin to alanine, and amino acid 96 in the light chain of MT01-L1 was mutated from tryptophan to phenylalanine. The resulting mutant antibodies are MT01-L1(M1), MT01-L1(M2), and MT01-L1(M1/M2).

In order to eliminate the ADCC and CDC activities of the antibody, the human IgG1 subtype of antibody heavy chain was replaced with human IgG2 subtype, resulting in the chimeric antibody MT01-L1(G2).

After humanization of the heavy and light chain variable regions of MT01-L1 and MT01-L1(G2), the humanized antibodies MT01-C1 and MT01-C1(G2) were obtained.

Example 2: Preparation of Antibodies

The cDNA sequences encoding the heavy chain and light chain of the fusion protein were cloned into the mammalian cell expression vectors pcDNA3.4, respectively. The heavy chain expression plasmid and the light chain expression plasmid at a molar ratio of 2:1 were transfected into HEK293 cells with Lipofectamine 2000 transfection reagent (Invitrogen), and cultured at 37° C. and 5% carbon dioxide for 7 days. The culture supernatants were collected, and the antibodies in the supernatants were purified by Protein A affinity chromatography. The purified antibodies were dialyzed in PBS solution and concentrated by freeze-drying, then stored at −20° C.

Example 3: ELISA Binding Assay

A 96-well high-affinity plate was coated at 100 μL/well with a protein solution having a concentration of 1 μg/mL, and shaken at 4° C. overnight. The next day, it was washed three times with 300 μL PBST (Tween 20: 0.5% o), then blocked with 5% BSA/PBS at 100 μL/well for 2 hours, and shaken at room temperature. After washing 3 times with 300 μL PBST, the gradient dilutions of samples were prepared with PBS, which were added into the 96-well plate at 100 μL/well and shaken at room temperature for 1 hour, and washed 3 times with 300 μL PBST. The secondary antibody goat anti-human IgG HRP solution was prepared, which was added into the 96-well plate at 100 μL/well, and shaken at room temperature for 1 hour. After washing 4 times with 300 μL PBST, TMB was added at 100 μL/well and developed for 20 min. 0.6N $H_2SO_4$ was added at 100 μL/well to stop the development, and OD450 nm was measured.

The measurement results are shown in FIG. 1. The EC50 values of ELISA binding for the human-mouse chimeric antibodies MT01-L1 and MT01-L2 were 290.7 ng/mL and 208.5 ng/mL, respectively.

Example 4: Binding with CHO-hOX40

Figure 2:
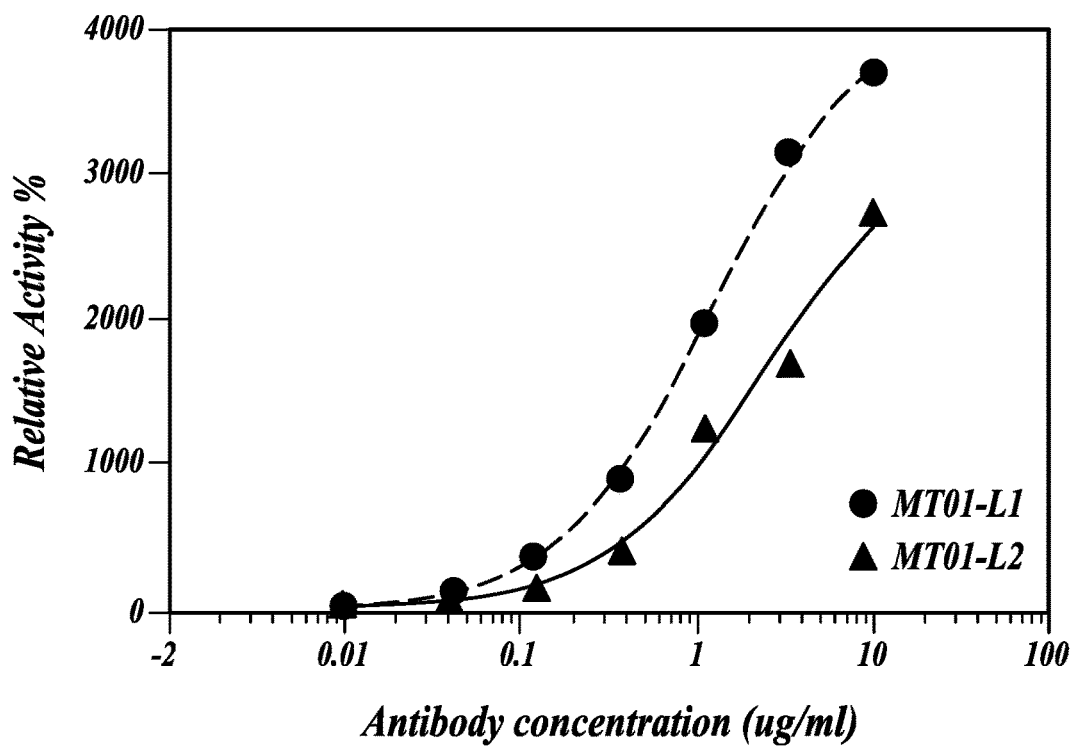
FIG. 2 shows the results of binding assay of the antibodies with CHO-hsOX40 by FACS detection.

The OX40 antibody gradient was created with PBS, and a stock solution of 10× final concentration was prepared. CHO-hOX40 cells were collected, washed once with PBS, counted, and diluted to a cell suspension of $2\times10^6$ cells/ml. 10 μl of OX40 antibody stock solutions were added into 100 μl of cell suspension, and incubated at 4° C. in the dark for 30 min. After washing twice with PBS, a secondary antibody was added and an incubation was carried out at 4° C. for 30 min in the dark. After washing once with PBS, the cells were suspended in 400 μl FACS buffer and measured on the instrument. As shown in FIG. 2, the results show that MT01-L1 and MT01-L2 bound to human OX40, and their EC50 values were 1.22 μg/mL and 2.42 μg/mL, respectively.

Figure 3:
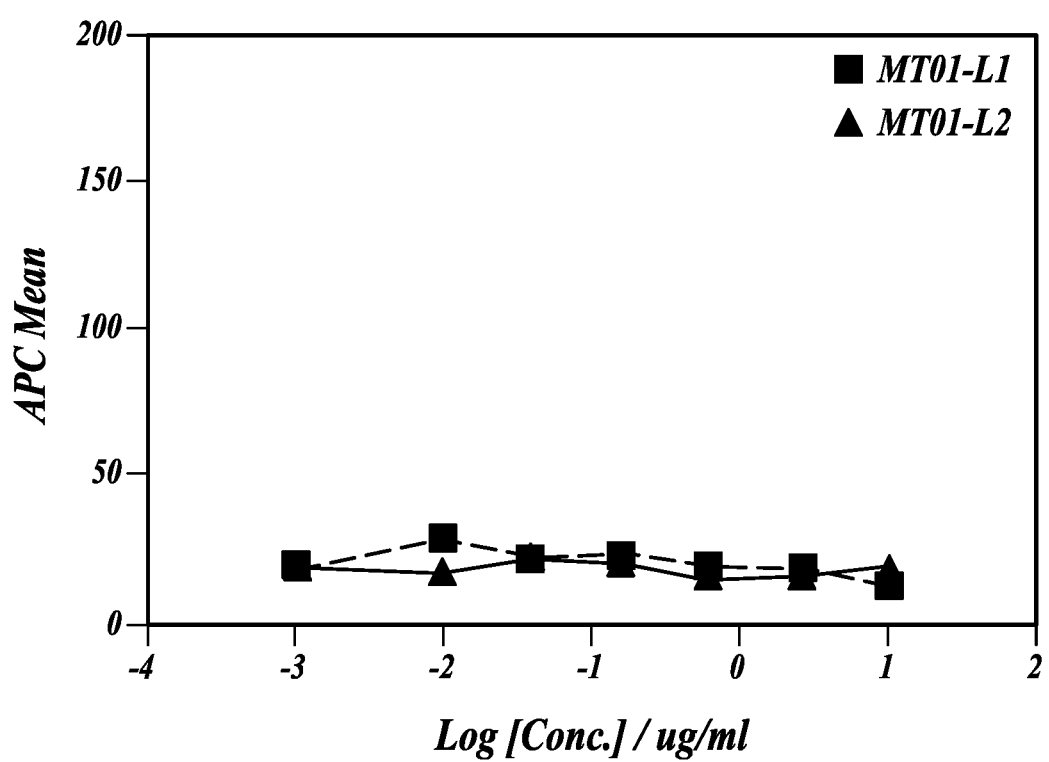
FIG. 3 shows the results of binding assay of the antibodies with CHO-mOX40 by FACS detection.

Similarly, the inventors of the present disclosure measured the binding of the antibodies to CHO cells expressing mouse OX40. Referring to the results of the binding assay in FIG. 3, it was found that neither MT01-L1 nor MT01-L2 bound to mouse OX40.

Example 5: Activation Assay of OX40 Signaling Pathway

The inventors of the present disclosure constructed a cell assay system for identifying the function of OX40 activating antibodies. Specifically, the inventors of the present disclosure constructed a cell line transfected stably by Jurkat-OX40-NFκB-luciferase reporter. When the OX40 activating antibodies are mixed with the stable transfected cell line and HEK293 cells overexpressing FcR, the OX40 antibodies can activate the expression of NFκB-luciferase reporter gene.

The OX40 antibody gradient was created with PBS, and a stock solution of 2× final concentration was prepared on ice. Jurkat-NFkB-luc-OX40 cells and HEK293 cells overexpressing FcR were collected, centrifuged and resuspended in the medium. The OX40 Abs and an appropriate amount of cell suspension were added into a 384-well plate. After an incubation of 5 hours, One-Glo (Promega) detection reagent was added. After mixing thoroughly, Pherastar was used to detect the fluorescent signals.

Figure 4A:
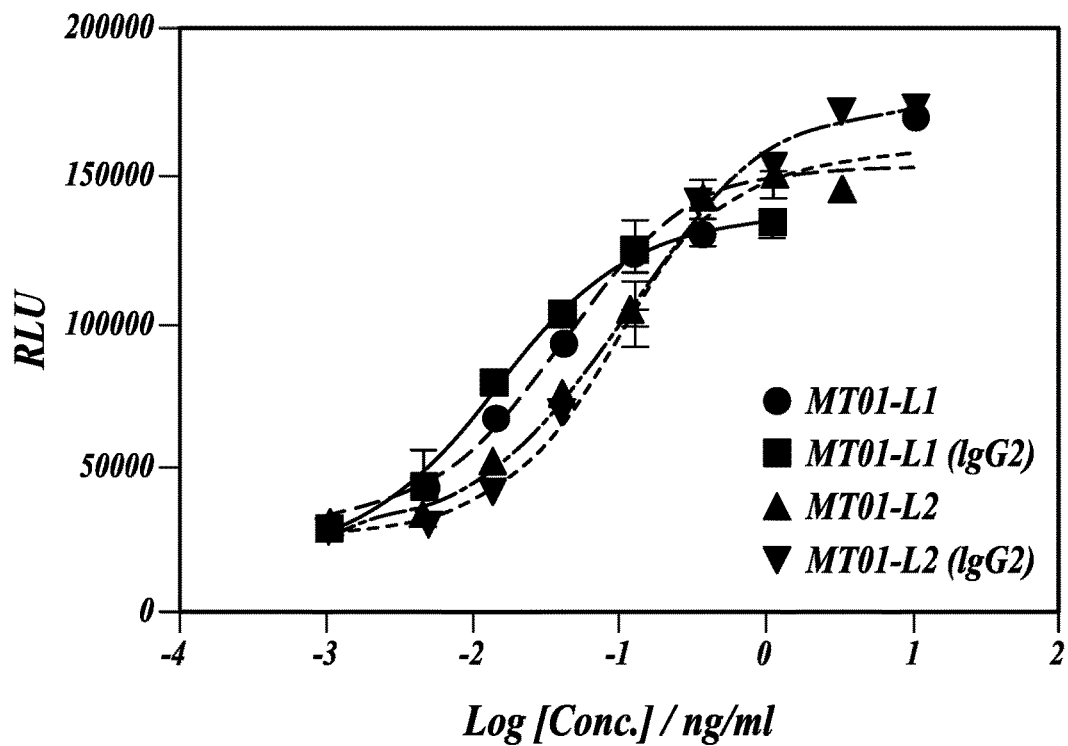
FIGS. 4A and 4B show that the OX40 antibodies activated the NF-kB signaling pathway activity in Jurkat cells.

As shown in FIG. 4A, the measured EC50 values of MT01-L1, MT01-L1(G2), MT01-L2 and MT01-L2(G2) in the above assay system for activation of the NFκB-luciferase reporter gene were 39.1, 14.9, 84.1 and 117.9 ng/mL, respectively.

Figure 4B:
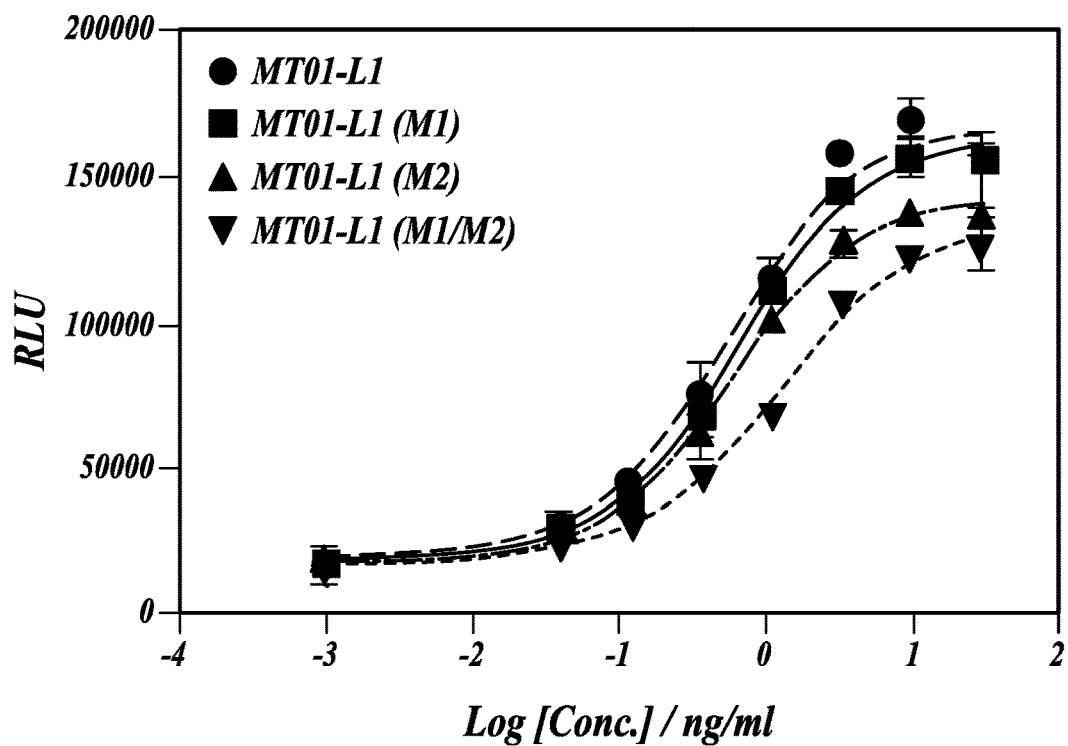

As shown in FIG. 4B, the measured EC50 values of MT01-L1, MT01-L1(M1), MT01-L1(M2) and MT01-L1 (M1/M2) in the above assay system for activation of the NFκB-luciferase reporter gene were 57.35, 64.52, 59.95 and 127.9 ng/mL, respectively.

Example 6: Competitive Assay with OX-40L

Figure 5:
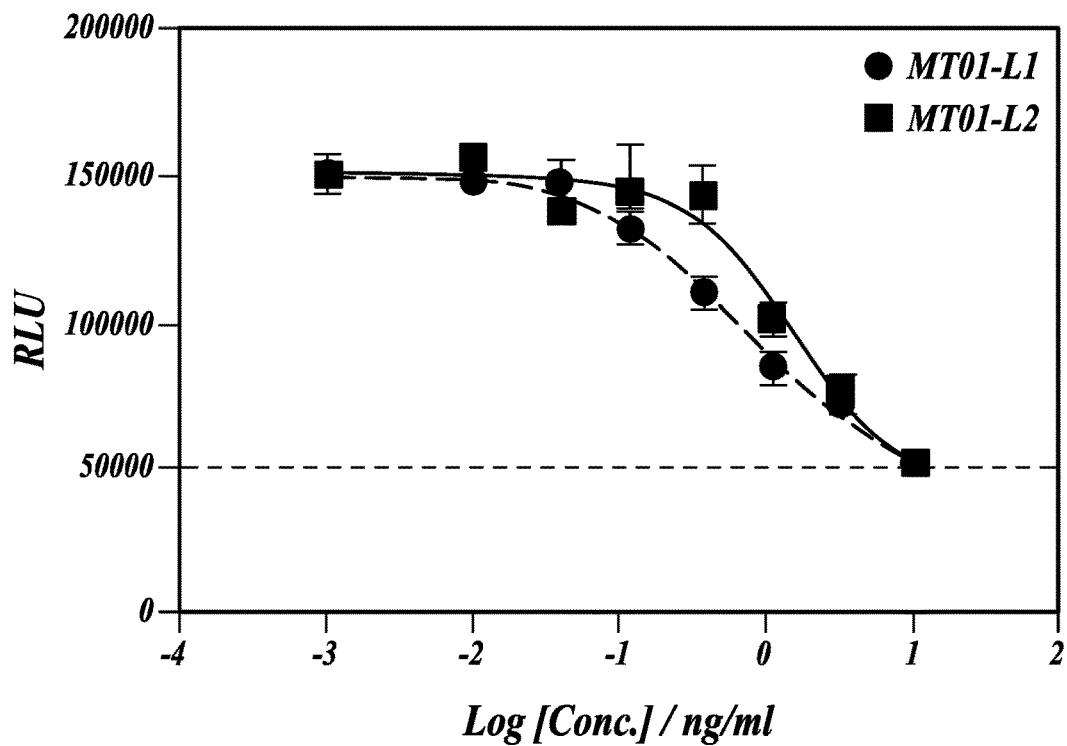
FIG. 5 shows that the OX40 antibodies competitively inhibited the OX40L-induced activation of NF-kB signaling pathway in Jurkat cells.

OX40L was diluted with PBS to prepare a stock solution of 10× final concentration, and an OX40 purified antibody gradient was created with PBS and a stock solution of 2× final concentration was prepared on ice. Jurkat-NFkB-luc-OX40 cells were collected, centrifuged and resuspended in the medium to prepare a cell suspension. The OX40 Abs, cell suspension and OX40L were added into a 384-well plate. After an incubation in an incubator at 37° C. and 5% $CO_2$ for 5 hours, One-Glo (Promega) reagent was added. After mixing thoroughly, Pherastar was used to measure fluorescent signals. As shown in FIG. 5, the results show that MT01-L1 and MT01-L2 inhibited the OX40L-induced activation of NFkB signaling pathway in Jurkat cells with IC50 of 0.686 μg/mL and 1.59 μg/mL, respectively.

Example 7: ADCC Assay

Figure 6:
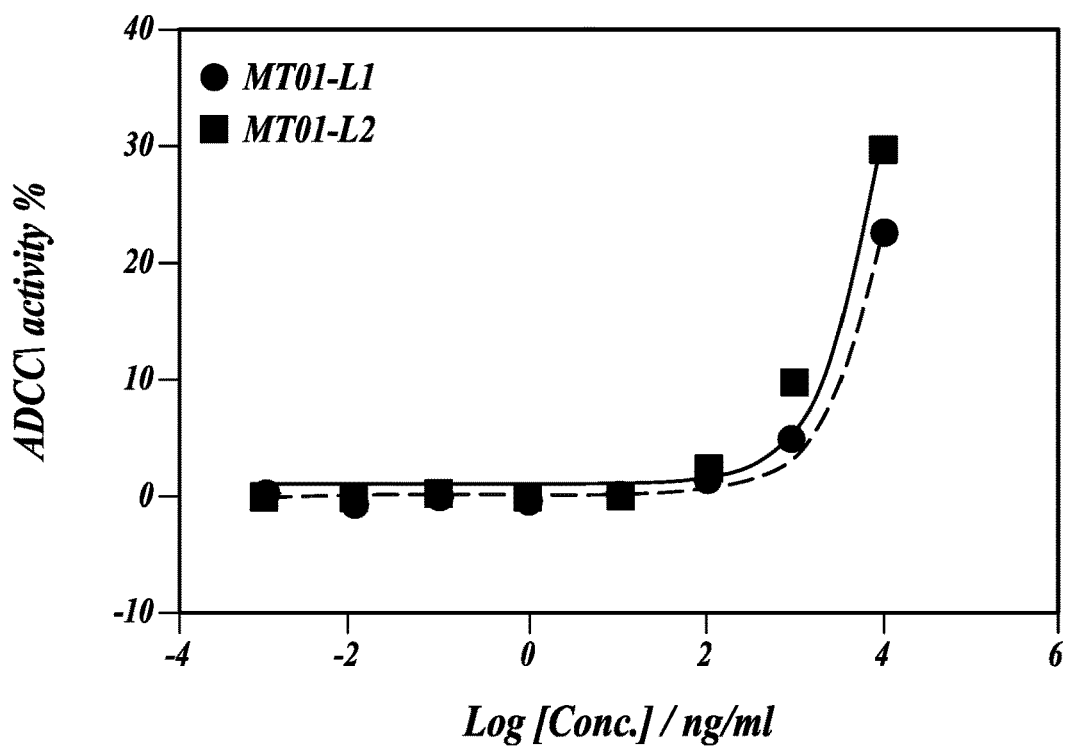
FIG. 6 shows the OX40 antibody-mediated ADCC effects of PBMC on CHO-OX40 cells.

CHO-OX40-luc was plated on a 96-well flat bottom plate and cultured overnight; the next day, an OX40 Ab gradient dilution was prepared with 1640 medium and added into the 96-well flat bottom plate. After adding human PBMC and co-incubating for 48 h, the supernatants were collected by centrifugation and assayed by Cyto-Tox Glo kit. As shown in FIG. 6, the results show that the chimeric antibodies MT01-L1 and MT01-L2 both had a significant ADCC effect at a concentration greater than 1 μg/mL.

Example 8: Promotion of Primary Th Cells Proliferation by OX40 Antibodies

Figure 7:
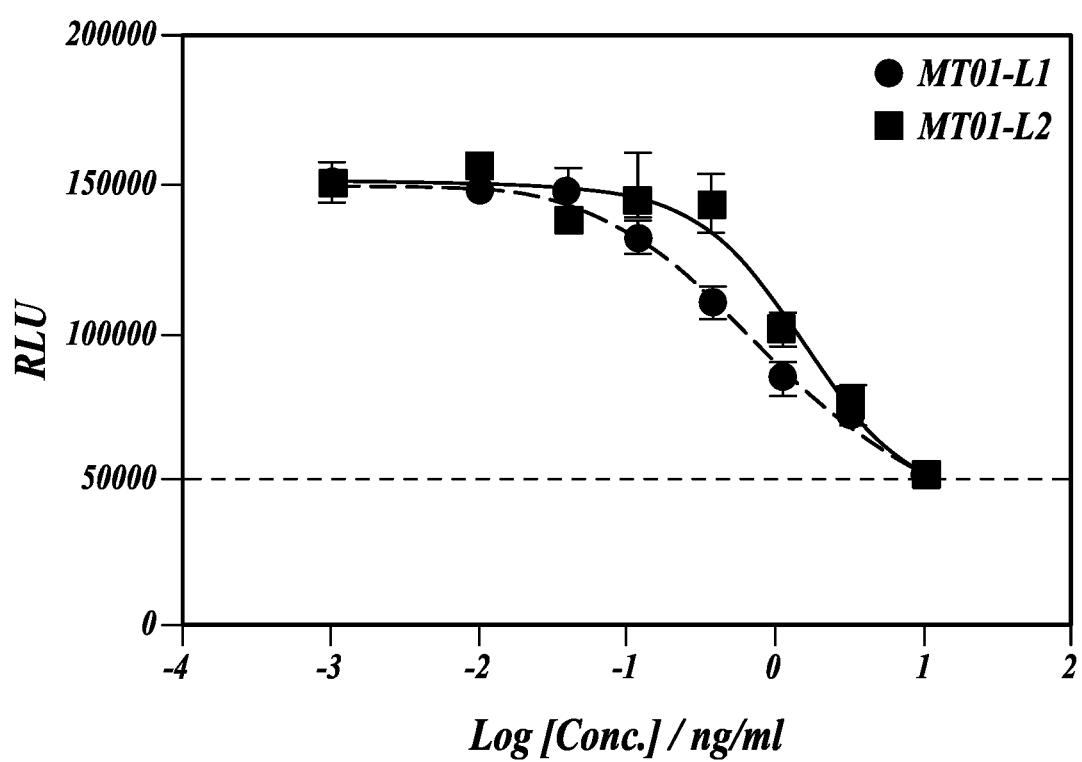
FIG. 7 shows that the OX40 antibodies promoted the proliferation of Th cells. Different concentrations of the OX40 antibodies and OKT3 functioned synergistically to promote the proliferation of CD4+Th cells.

CD4+ cells were isolated from the blood of healthy volunteers and cultured in 1640 complete medium containing PHA/IL-2 for two days before use. A high-affinity 96-well round bottom plate was coated with OKT3 (0.1 μg/well) and the serially diluted OX40 antibodies or control IgG. The next day, the well plate was washed twice with PBS, and pre-treated CD4+ cells were added into the 96-well plate pre-coated with the antibodies at 50,000 cells per well. After 7 days of subsequent culture, cell proliferation was detected with CCK8 kit. As shown in FIG. 7, the results of assay show that in the presence of OKT3 antibody, the OX40 antibodies can promote the proliferation of CD4 Th cells in a dose-dependent manner. Also, with respect to the CD4+ cells to which only the highest concentration of OX40 antibodies at 1500 ng/mL were added, the viability was measured in the assay and taken as the base on which the data were normalized.

Example 9: Pharmacodynamic Study of Chimeric Antibodies in Animals

Figure 8A:
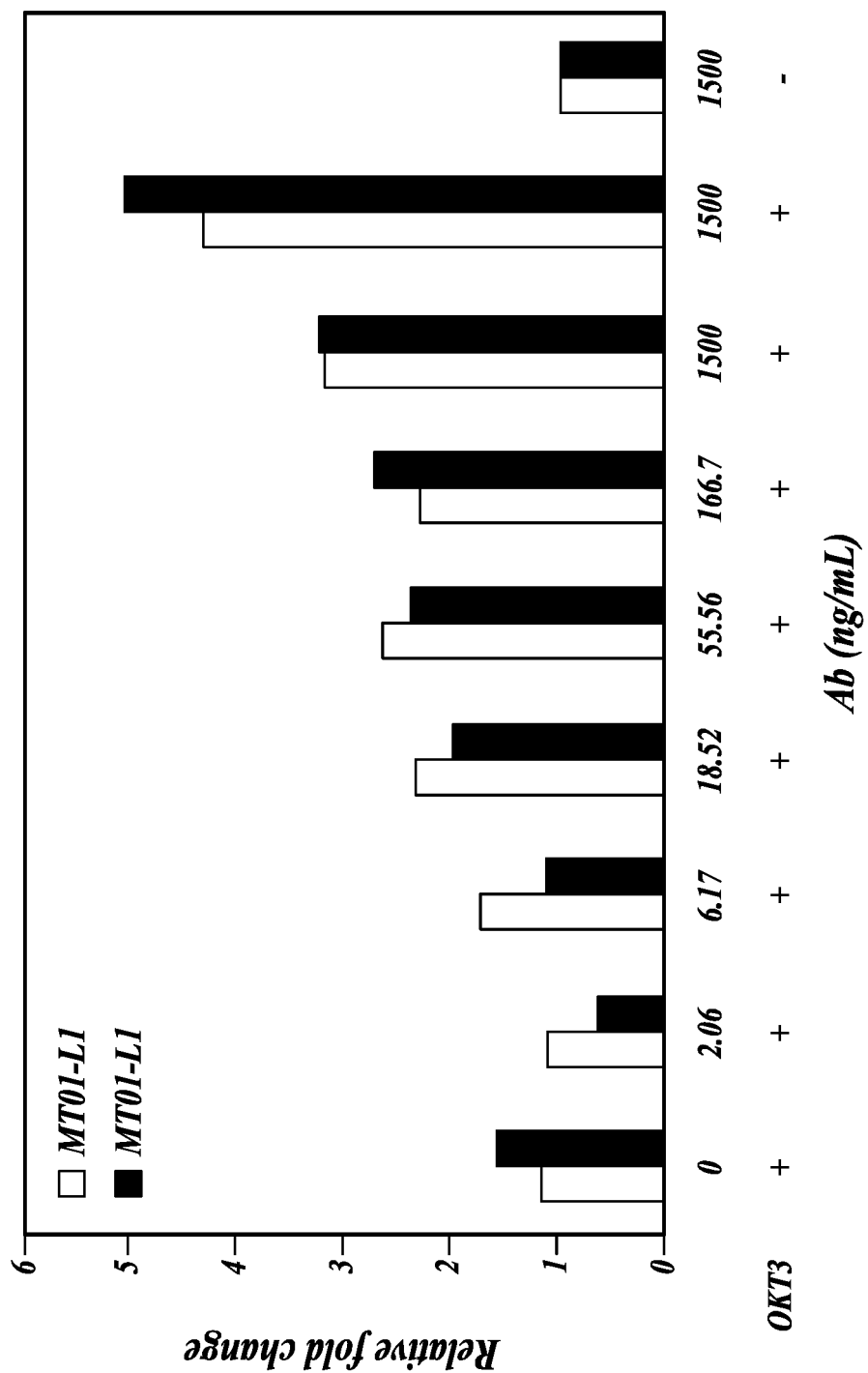
FIG. 8A is a graph showing the relationship between the OX40 antibody drugs and the inhibition of tumor volume (** $P < 0.01$)
Figure 8B:
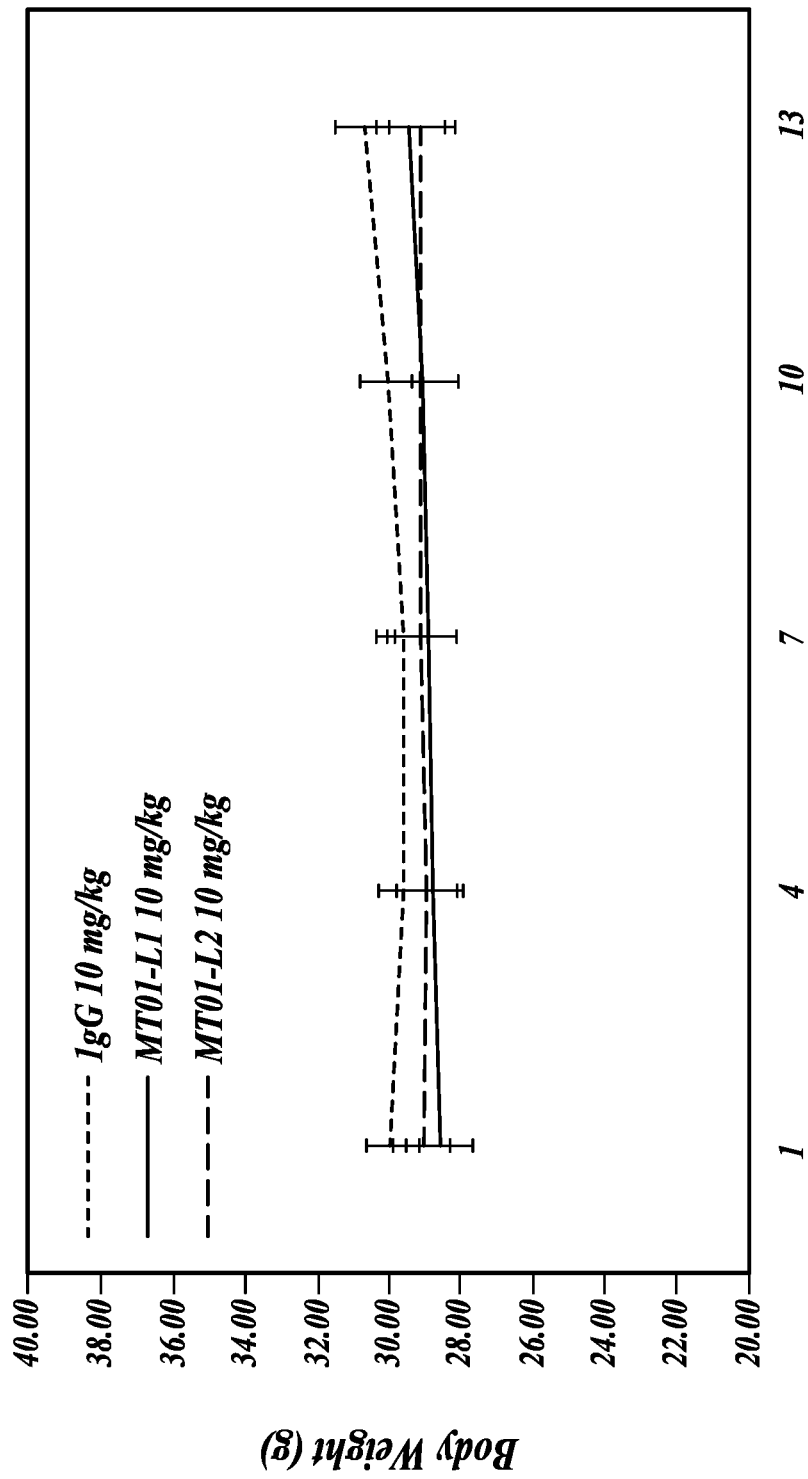
FIG. 8B shows that the OX40 antibody drugs have no significant impact on the body weight of mice.

Mouse colon cancer cells were inoculated subcutaneously into OX40 humanized mice (the OX40 extracellular segment was replaced with the human OX40 extracellular segment sequence) at an amount of $10^6$ cells per mouse. After the tumor grew to about 100 mm³, the OX40 antibodies or IgG1 control (10 mg/kg) was administered intravenously once every 3 days, for a total of 4 administrations. As shown by the results in FIG. 8A and FIG. 8B, after 13 days from the start of administration, MT01-L1 had an extremely significant efficacy compared with the control group. Under the same dosing regimen, although the efficacy of MT01-L2 did not reach a statistically significant difference, it also showed an obvious trend in efficacy.

Example 10: Activities of Humanized Antibodies

Humanized antibodies MT01-C1 and MT01-C1(G2) were obtained through CDR grafting onto and amino acid back-mutation of the chimeric antibodies.

The in vitro binding assay of humanized antibodies and human OX antigen protein was carried out as described in Example 3. The results show that the EC50 values of ELISA binding for humanized antibodies and human OX40 protein were 0.345 μg/mL and 0.390 μg/mL, respectively.

Figure 9A:
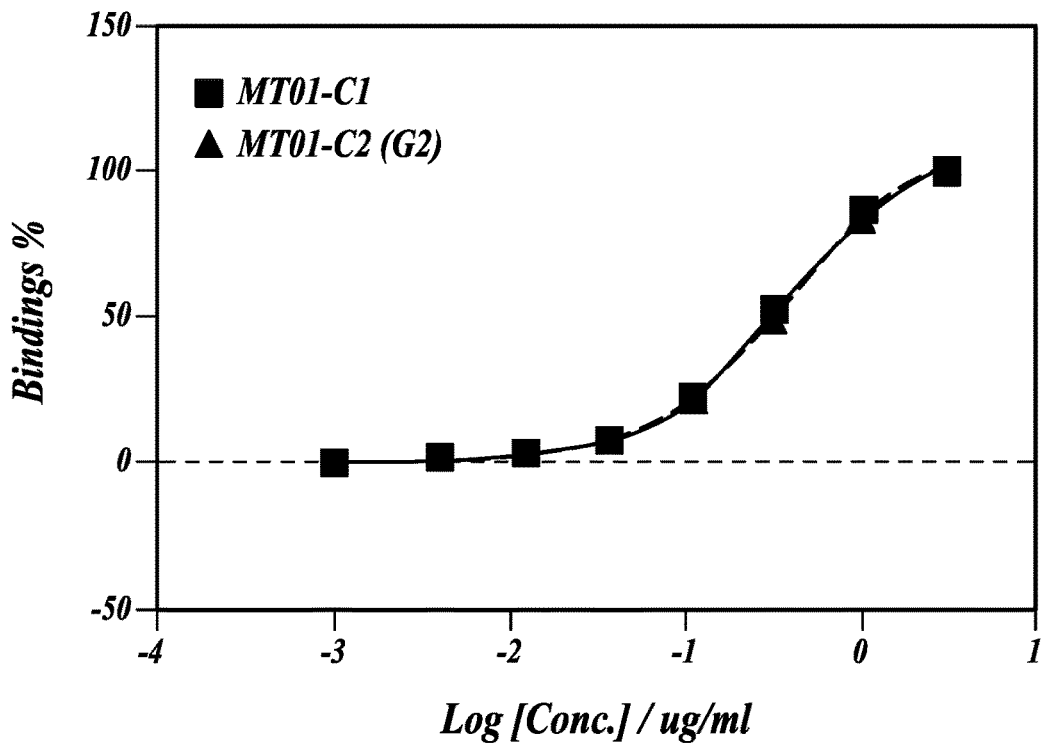
FIG. 9A shows the ELISA data of the humanized antibodies binding to human OX40.
Figure 9B:
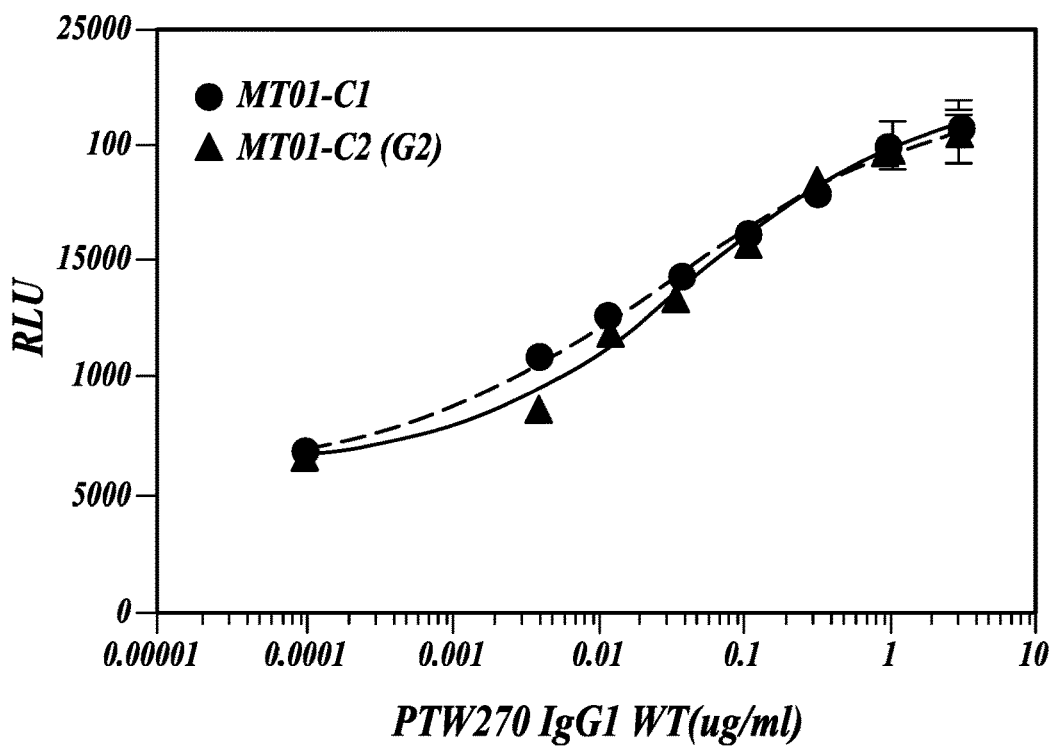
FIG. 9B shows the activation activities of the humanized antibodies on NF-kB signaling pathway in Jurkat cells.

The in vitro activity assay of humanized antibodies was carried out as described in Example 5. The results show that the EC50s values of activation for MT01-C1 and MT01-C1 (G2) on a cell line transfected stably by Jurkat-OX40-NFκB-luciferase reporter were 0.028 and 0.0434 μg/mL, respectively (FIG. 9B).

Figure 9C:
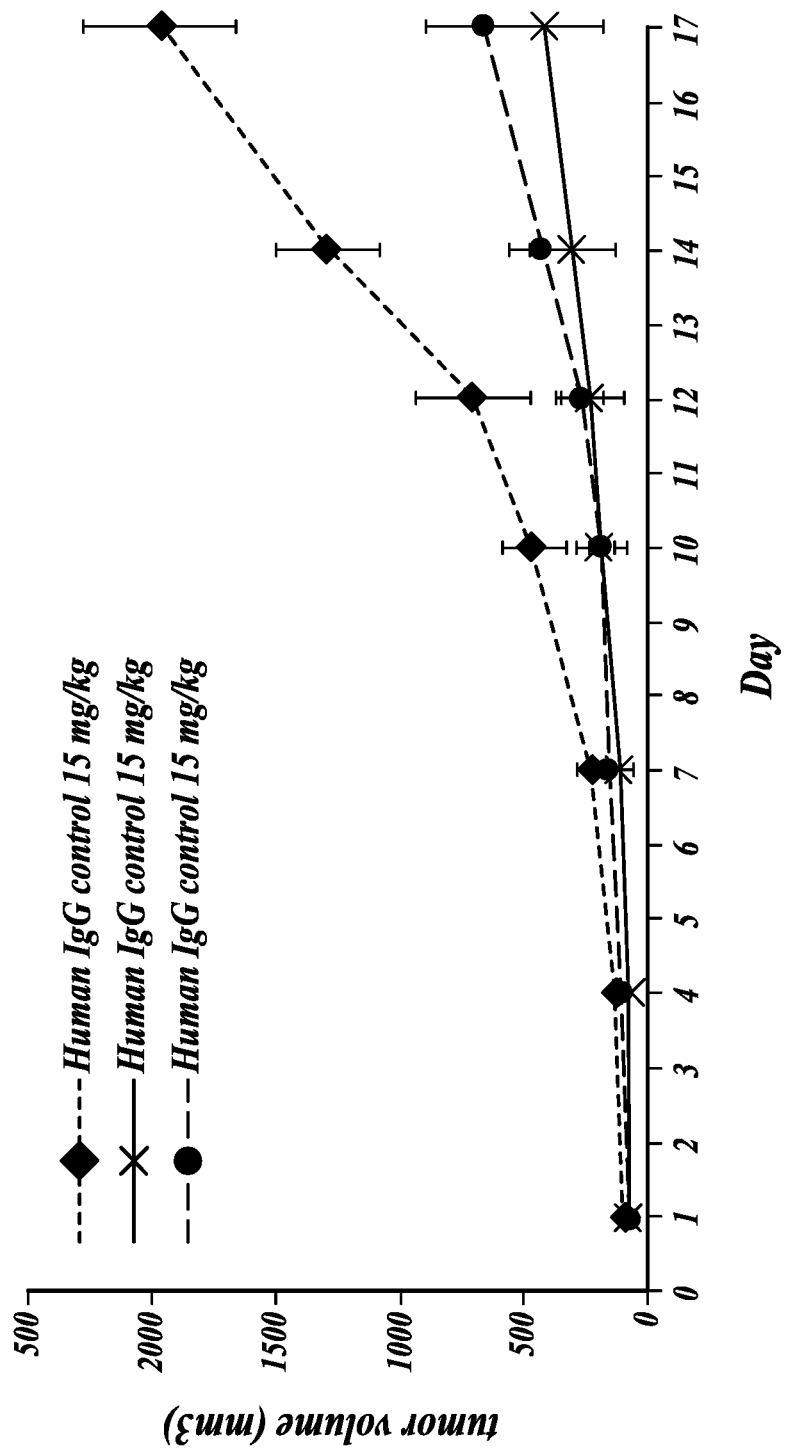
FIG. 9C shows the anti-tumor effects of the humanized antibodies on the OX40-humanized transgenic mice.

The pharmacodynamic study of humanized antibodies in animals was carried out as that in Example 8, with the exception that the administration mode of antibodies was changed to 15 mg/kg, a single administration. The results show that 17 days after administration, the inhibition rates of MT01-C1 and MT01-C1(G2) on tumor volume reached 79% and 66%, respectively (FIG. 9C).

Example 11: PK Properties of Humanized Antibodies in Mice and Cynomolgus Monkeys In the PK experiment in mice, each antibody was injected intravenously into C56BL6 female mice (6 mice in each group) at a dose of 5 mg/kg. 1 h, 2 h, 6 h, 24 h, 48 h, 72 h, 96 h, 192 h and 312 h after the administration, 100 μL blood samples were taken from 3 mice in each group at each time point. After standing at 4° C. for 2-3 h, the blood samples were centrifuged at 5000 rpm for 10 min. The serums were collected and stored at −80° C. for ELISA assay.

To measure the antibody concentration in serum, a high affinity microplate was coated with human OX40 antigen. Mouse serum samples were diluted at 1:100 in dilution buffer and then added into the wells. MT01-C1 and MT01-C1(G2) in C57BL6 mouse serums bound to the human OX40-6his coated in the microplate, and unbound drugs were washed away in the washing step.

Then donkey anti-human IgG labeled with horseradish peroxidase (HRP) was added, which bound to the antigen-antibody complex. After washing, HRP enzyme substrate (TMB) was added to produce a color reaction, with the shades of color being proportional to the concentrations of the antibodies to be tested. After stopping the reaction with 1M $H_2SO_4$, the OD values were read by a microplate reader with a measuring wavelength of 450 nm and a reference wavelength of 620 nm. The concentrations of the antibodies to be tested in the biological sample were calculated by comparing the OD450 nm reads with the standard curve of the sample.

Figure 10A:
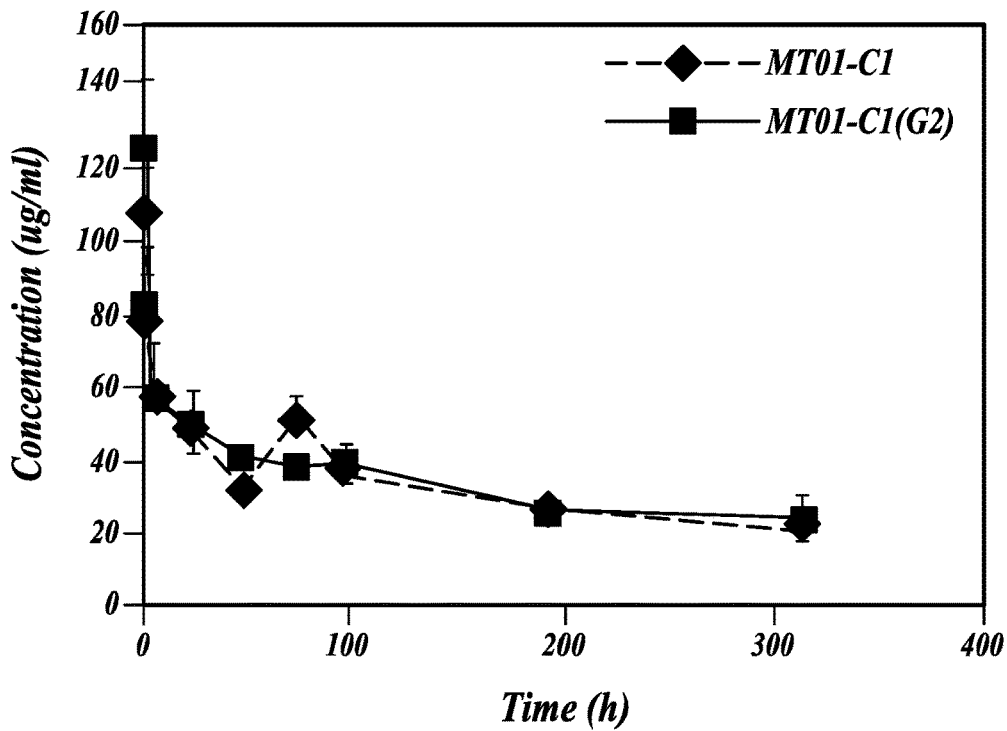
FIG. 10A shows the pharmacokinetic performances of the OX40 antibody drugs in mice.

The measurement results show that the Cmax of MT01-C1 and MT01-C1(G2) were 125.7 μg/mL and 107.2 μg/mL, respectively, and $t_{1/2}$ were 265 hrs and 321 hrs, respectively (FIG. 10A).

In the PK experiment in cynomolgus monkeys, each antibody was injected intravenously into male cynomolgus monkeys (3 monkeys in each group) at a dose of 1.5 mg/kg. 48 h before the administration, and 15 min, 30 min, 1 h, 2 h, 6 h, 24 h, 48 h, 72 h, 96 h, 168 h, 240 h, 336 h and 504 h after the administration, 100 μL blood samples were taken at each time point. After standing at 4° C. for 2-3 h, the blood samples were centrifuged at 5000 rpm for 10 min. The serums were collected and stored at −80° C. for ELISA assay.

To measure the antibody concentration in serum, a high affinity microplate was coated with human OX40 antigen. Cynomolgus monkey serum samples were diluted at 1:100 in dilution buffer and added into the wells. MT01-C1 and MT01-C1(G2) in cynomolgus monkey serums bound to the human OX40-6his coated in the microplate, and the unbound drugs were washed away in the washing step. Then donkey anti-human IgG labeled with horseradish peroxidase (HRP) was added, which bound to the antigen-antibody complexes. After washing, HRP enzyme substrate (TMB) was added to produce a color reaction, with the shades of color being proportional to the concentrations of the antibodies to be tested. After stopping the reaction with 1M $H_2SO_4$, the OD values were read by a microplate reader with a measuring wavelength of 450 nm and a reference wavelength of 620 nm. The concentrations of the antibodies to be tested in the biological sample were calculated by comparing the OD450 nm reads with the standard curve of the sample.

Figure 10B:
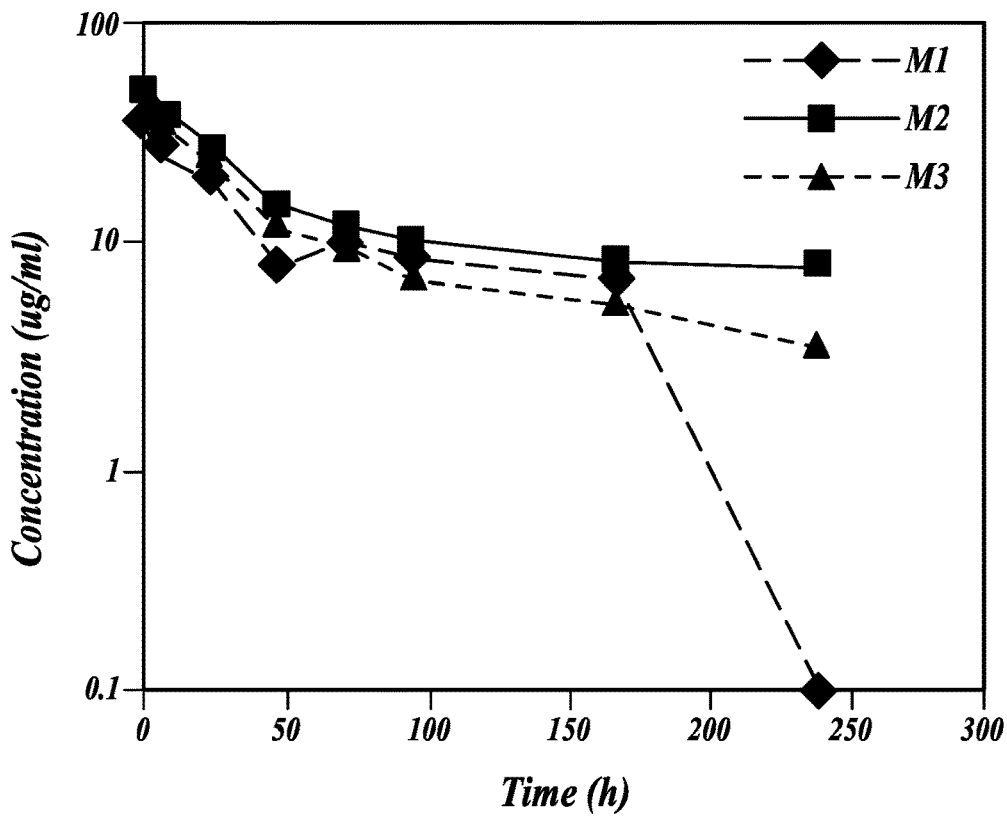
FIG. 10B shows the pharmacokinetic performances of the OX40 antibody drugs in cynomolgus monkeys.

The measurement results show that after 1.5 mg/kg intravenous injection into cynomolgus monkeys, the terminal phase elimination $t_{1/2}$ was 121.307±66.853 hrs, and Cmax was 42.619±3.464 μg/mL (FIG. 10B).

The above are only the preferred examples of the present disclosure and do not serve to limit the present disclosure in any way. Without departing from the scope of the technical solutions of the present disclosure, any skilled person in the technical field to which the present disclosure pertains may make any form of equivalent replacement or modification of the technical solutions and technical contents disclosed herein, which belongs to the contents which do not depart from the technical solutions of the present disclosure, and still falls within the scope of the present disclosure.

The invention claimed is:

1. An isolated antibody or antigen binding fragment thereof, comprising a heavy chain complementary determining region and a light chain complementary determining region, wherein the heavy chain complementary determining region is selected from one of: SEQ ID NO: 1 or SEQ ID NO:9; SEQ ID NO:2, SEQ ID NO:7, or SEQ ID NO:10; and SEQ ID NO:3 or SEQ ID NO: 11; and/or the light chain complementary determining region is selected from: SEQ ID NO: 4 or SEQ ID NO:12; SEQ ID NO:5 or SEQ ID NO:13; and SEQ ID NO:6, SEQ ID NO:8, or SEQ ID NO: 14.

2. The isolated antibody or antigen binding fragment thereof according to claim 1, wherein the heavy chain complementary determining region is:
   SEQ ID NO: 1, SEQ ID NO: 2, and SEQ ID NO: 3;
   SEQ ID NO: 1, SEQ ID NO: 7, and SEQ ID NO: 3; or
   SEQ ID NO: 9, SEQ ID NO: 10, and SEQ ID NO: 11; and/or
   the light chain complementary determining region is:
   SEQ ID NO: 4, SEQ ID NO: 5, and SEQ ID NO: 6;
   SEQ ID NO: 4, SEQ ID NO: 5, and SEQ ID NO: 8; or
   SEQ ID NO: 12, SEQ ID NO: 13, and SEQ ID NO: 14.

3. The isolated antibody or antigen binding fragment thereof according to claim 1, wherein:
   the heavy chain complementary determining region comprises SEQ ID NO: 1, SEQ ID NO: 2, and SEQ ID NO: 3, and the light chain complementary determining region comprises SEQ ID NO: 4, SEQ ID NO: 5, and SEQ ID NO: 6;
   the heavy chain complementary determining region comprises SEQ ID NO: 1, SEQ ID NO: 7, and SEQ ID NO: 3, and the light chain complementary determining region comprises SEQ ID NO: 4, SEQ ID NO: 5, and SEQ ID NO: 6;
   the heavy chain complementary determining region comprises SEQ ID NO: 1, SEQ ID NO: 2, and SEQ ID NO: 3, and the light chain complementary determining region comprises SEQ ID NO: 4, SEQ ID NO: 5, and SEQ ID NO: 8;
   the heavy chain complementary determining region comprises SEQ ID NO: 1, SEQ ID NO: 7, and SEQ ID NO: 3, and the light chain complementary determining region comprises SEQ ID NO: 4, SEQ ID NO: 5, and SEQ ID NO: 8; or
   the heavy chain complementary determining region comprises SEQ ID NO: 9, SEQ ID NO: 10, and SEQ ID NO: 11, and the light chain complementary determining region comprises SEQ ID NO: 12, SEQ ID NO: 13, and SEQ ID NO: 14; and wherein each of the isolated antibody or antigen binding fragments thereof specifically bind OX40.

4. The isolated antibody or antigen binding fragment thereof according to claim 1, wherein the heavy chain variable region is replaced with the following sequences: SEQ ID NO: 15, SEQ ID NO: 17, SEQ ID NO: 19, or SEQ ID NO: 29; and/or the light chain variable region is replaced by the following sequences: SEQ ID NO: 16, SEQ ID NO: 18, SEQ ID NO: 20, or SEQ ID NO: 30.

5. The isolated antibody or antigen binding fragment thereof according to claim 4, wherein,
   the heavy chain complementary determining region comprises SEQ ID NO: 15, and the light chain complementary determining region comprises SEQ ID NO: 16;
   the heavy chain complementary determining region comprises SEQ ID NO: 17, and the light chain complementary determining region comprises SEQ ID NO: 16;
   the heavy chain complementary determining region comprises SEQ ID NO: 15, and the light chain complementary determining region comprises SEQ ID NO: 18;
   the heavy chain complementary determining region comprises SEQ ID NO: 17, and the light chain complementary determining region comprises SEQ ID NO: 18; or
   the heavy chain complementary determining region comprises SEQ ID NO: 19, and the light chain complementary determining region comprises SEQ ID NO: 20; and wherein the isolated antibody or antigen fragment thereof specifically binds OX40.

6. The isolated antibody or antigen binding fragment thereof according to claim 3, which is a humanized or fully human monoclonal antibody.

7. The isolated antibody or antigen binding fragment thereof according to claim 3, which is a camelized single domain antibody, a bifunctional antibody, a scFv, a scFv dimer, a BsFv, a dsFv, a dsFv$_2$, a dsFv-dsFv', an Fv fragment, an Fab, an Fab', an F(ab')$_2$, a ds bifunctional antibody, a nanobody, a domain antibody or a bivalent domain antibody.

8. The isolated antibody or antigen binding fragment thereof according to claim 3, further comprising an immunoglobulin constant region which includes a constant region of human IgG1, IgG2, or IgG4 protein.

9. The isolated antibody or antigen binding fragment thereof according to claim 3, further comprising a conjugate.

10. An isolated polynucleotide encoding the antibody or antigen binding fragment thereof according to claim 1.

11. A vector comprising the isolated polynucleotide according to claim 10.

12. A host cell comprising the vector according to claim 11.

13. A method for expressing an antibody or antigen binding fragment thereof according to claim 1, comprising culturing a host cell comprising a vector comprising an isolated polynucleotide sequence encoding the antibody or antigen fragment thereof under the conditions for expressing the isolated polynucleotide.

14. A kit comprising an antibody or antigen binding fragment thereof according to claim 3.

15. A pharmaceutical composition comprising an antibody or antigen binding fragment thereof according to claim 3, and one or more pharmaceutically acceptable carriers.

16. A method for detecting the presence or level of human or monkey OX40, comprising contacting an antibody or antigen binding fragment thereof according to claim 3 with a biological sample and detecting the presence or level of antibody binding in the sample.

17. A method for detecting and identifying an individual with an increased level of OX40, comprising contacting an antibody or antigen binding fragment thereof according to claim 3 with a biological sample and comparing the level of antibody binding detected with a standard control.

18. A method for monitoring the level of an immune response during an OX40 agonist treatment, comprising using contacting an antibody or antigen binding fragment thereof according to claim 3 with a biological sample and detecting a decrease in the level of antibody or antigen binding fragment in the sample.

19. A method for inducing an up-regulated immune response in a subject, comprising administering the antibody or antigen binding fragment thereof according to claim 3.

20. The method according to claim 19, wherein the up-regulated immune response is in a subject with cancer or a chronic viral infection.

21. The isolated antibody or antigen binding fragment thereof according to claim 5, which is a humanized or fully human monoclonal antibody.

22. The isolated antibody or antigen binding fragment thereof according to claim 5, which is a camelized single domain antibody, a bifunctional antibody, a scFv, a scFv dimer, a BsFv, a dsFv, a $dsFv_2$, a dsFv-dsFv', an Fv fragment, an Fab, an Fab', an $F(ab')_2$, a ds bifunctional antibody, a nanobody, a domain antibody or a bivalent domain antibody.

23. The isolated antibody or antigen binding fragment thereof according to claim 5, further comprising an immunoglobulin constant region which includes a constant region of human IgG1, IgG2, or IgG4 protein.

24. The isolated antibody or antigen binding fragment thereof according to claim 5, further comprising a conjugate.

25. A kit comprising an antibody or antigen binding fragment thereof according to claim 5.

26. The pharmaceutical composition comprising an antibody or antigen binding fragment thereof according to claim 6, and one or more pharmaceutically acceptable carriers.

27. The pharmaceutical composition comprising an antibody or antigen binding fragment thereof according to claim 7, and one or more pharmaceutically acceptable carriers.

28. The pharmaceutical composition comprising an antibody or antigen binding fragment thereof according to claim 8, and one or more pharmaceutically acceptable carriers.

29. The pharmaceutical composition comprising an antibody or antigen binding fragment thereof according to claim 9, and one or more pharmaceutically acceptable carriers.

30. A method for detecting the presence or level of human or monkey OX40, comprising contacting an antibody or antigen binding fragment thereof according to claim 5 with a biological sample and detecting the presence or level of antibody or antigen binding fragment binding in the sample.

31. A method for detecting and identifying an individual suffering from a disorder or a condition responsive to an OX40 agonist with an increased level of OX40, comprising contacting an antibody or antigen binding fragment thereof according to claim 5 with a biological sample and comparing the level of antibody binding detected with a standard control.

32. A method for monitoring the level of an immune response during an OX40 agonist treatment, comprising contacting an antibody or antigen binding fragment thereof according to claim 5 with a biological sample and detecting a decrease in the level of antibody or antigen binding fragment in the sample.

33. A method for inducing an up-regulated immune response in a subject, comprising administering the antibody or antigen binding fragment thereof according to claim 5.

34. The method according to claim 33, wherein the up-regulated immune response is in a subject with cancer or a chronic viral infection.

* * * * *

SEQUENCE LISTING

```
<160> NUMBER OF SEQ ID NOS: 33

<210> SEQ ID NO 1
<211> LENGTH: 10
<212> TYPE: PRT
<213> ORGANISM: artificial sequence
<220> FEATURE:
<223> OTHER INFORMATION: Synthetic

<400> SEQUENCE: 1

Gly Tyr Thr Phe Thr Ser Tyr Val Met His
1               5                   10

<210> SEQ ID NO 2
<211> LENGTH: 17
<212> TYPE: PRT
<213> ORGANISM: artificial sequence
<220> FEATURE:
<223> OTHER INFORMATION: Synthetic

<400> SEQUENCE: 2

Tyr Ile Asn Pro Tyr Asn Asp Gly Thr Lys Tyr Asn Glu Lys Phe Lys
1               5                   10                  15

Gly

<210> SEQ ID NO 3
<211> LENGTH: 12
<212> TYPE: PRT
<213> ORGANISM: artificial sequence
<220> FEATURE:
<223> OTHER INFORMATION: Synthetic

<400> SEQUENCE: 3

Ala Asn Tyr Tyr Gly Ser Lys Phe Ala Met Asp Tyr
1               5                   10

<210> SEQ ID NO 4
<211> LENGTH: 11
<212> TYPE: PRT
<213> ORGANISM: artificial sequence
<220> FEATURE:
<223> OTHER INFORMATION: Synthetic
```

<400> SEQUENCE: 4

Arg Ala Ser Gln Asp Ile Ser Asn Tyr Leu Ser
1               5                   10

<210> SEQ ID NO 5
<211> LENGTH: 7
<212> TYPE: PRT
<213> ORGANISM: artificial sequence
<220> FEATURE:
<223> OTHER INFORMATION: Synthetic

<400> SEQUENCE: 5

Tyr Thr Ser Arg Leu His Ser
1               5

<210> SEQ ID NO 6
<211> LENGTH: 9
<212> TYPE: PRT
<213> ORGANISM: artificial sequence
<220> FEATURE:
<223> OTHER INFORMATION: Synthetic

<400> SEQUENCE: 6

Gln Gln Gly Ile Thr Leu Pro Trp Thr
1               5

<210> SEQ ID NO 7
<211> LENGTH: 17
<212> TYPE: PRT
<213> ORGANISM: artificial sequence
<220> FEATURE:
<223> OTHER INFORMATION: Synthetic

<400> SEQUENCE: 7

Tyr Ile Asn Pro Tyr Asn Asp Ala Thr Lys Tyr Asn Glu Lys Phe Lys
1               5                   10                  15

Gly

<210> SEQ ID NO 8
<211> LENGTH: 9
<212> TYPE: PRT
<213> ORGANISM: artificial sequence
<220> FEATURE:
<223> OTHER INFORMATION: Synthetic

<400> SEQUENCE: 8

Gln Gln Gly Ile Thr Leu Pro Phe Thr
1               5

<210> SEQ ID NO 9
<211> LENGTH: 10
<212> TYPE: PRT
<213> ORGANISM: artificial sequence
<220> FEATURE:
<223> OTHER INFORMATION: Synthetic

<400> SEQUENCE: 9

Gly Phe Thr Phe Asn Thr Tyr Ala Met Asn
1               5                   10

<210> SEQ ID NO 10
<211> LENGTH: 19
<212> TYPE: PRT
<213> ORGANISM: artificial sequence
<220> FEATURE:
<223> OTHER INFORMATION: Synthetic

```
<400> SEQUENCE: 10

Arg Ile Arg Ser Lys Ser Asn Asn Tyr Ala Thr Tyr Tyr Ala Asp Ser
1               5                   10                  15

Val Lys Asp

<210> SEQ ID NO 11
<211> LENGTH: 10
<212> TYPE: PRT
<213> ORGANISM: artificial sequence
<220> FEATURE:
<223> OTHER INFORMATION: Synthetic

<400> SEQUENCE: 11

Val Arg Ser Leu Gly Arg Ala Phe Val Tyr
1               5                   10

<210> SEQ ID NO 12
<211> LENGTH: 12
<212> TYPE: PRT
<213> ORGANISM: artificial sequence
<220> FEATURE:
<223> OTHER INFORMATION: Synthetic

<400> SEQUENCE: 12

Thr Leu Ser Ser Gln His Ser Thr Tyr Ile Ile Glu
1               5                   10

<210> SEQ ID NO 13
<211> LENGTH: 8
<212> TYPE: PRT
<213> ORGANISM: artificial sequence
<220> FEATURE:
<223> OTHER INFORMATION: Synthetic

<400> SEQUENCE: 13

Glu Leu Lys Lys Asp Gly Ser His
1               5

<210> SEQ ID NO 14
<211> LENGTH: 13
<212> TYPE: PRT
<213> ORGANISM: artificial sequence
<220> FEATURE:
<223> OTHER INFORMATION: Synthetic

<400> SEQUENCE: 14

Gly Val Gly Asn Thr Ile Lys Glu Gln Phe Val Tyr Val
1               5                   10

<210> SEQ ID NO 15
<211> LENGTH: 119
<212> TYPE: PRT
<213> ORGANISM: artificial sequence
<220> FEATURE:
<223> OTHER INFORMATION: Synthetic

<400> SEQUENCE: 15

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Leu Lys Gln Lys Pro Gly Gln Gly Leu Glu Trp Ile
            35                  40                  45
```

```
Gly Tyr Ile Asn Pro Tyr Asn Asp Gly Thr Lys Tyr Asn Glu Lys Phe
        50                  55                  60

Lys Gly Lys Ala Lys Leu Thr Ser Asp Lys Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Asn Tyr Tyr Gly Ser Lys Phe Ala Met Asp Tyr Trp Gly Gln Gly
                100                 105                 110

Thr Ser Val Thr Val Ser Ser
            115
```

<210> SEQ ID NO 16
<211> LENGTH: 107
<212> TYPE: PRT
<213> ORGANISM: artificial sequence
<220> FEATURE:
<223> OTHER INFORMATION: Synthetic

<400> SEQUENCE: 16

```
Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn Tyr
                20                  25                  30

Leu Ser Trp Tyr Gln Arg Lys Pro Asp Gly Ala Val Lys Leu Leu Ile
             35                  40                  45

Tyr Tyr Thr Ser Arg Leu His Ser Gly Val Pro Ser Arg Phe Ser Gly
 50                  55                  60

Ser Gly Ser Gly Ala Asp Tyr Ser Leu Thr Ile Ser Asn Leu Glu Gln
 65                  70                  75                  80

Glu Asp Ile Ala Thr Tyr Phe Cys Gln Gln Gly Ile Thr Leu Pro Trp
                 85                  90                  95

Thr Phe Gly Gly Gly Thr Lys Leu Glu Ile Lys
            100                 105
```

<210> SEQ ID NO 17
<211> LENGTH: 119
<212> TYPE: PRT
<213> ORGANISM: artificial sequence
<220> FEATURE:
<223> OTHER INFORMATION: Synthetic

<400> SEQUENCE: 17

```
Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
                20                  25                  30

Val Met His Trp Leu Lys Gln Lys Pro Gly Gln Gly Leu Glu Trp Ile
             35                  40                  45

Gly Tyr Ile Asn Pro Tyr Asn Asp Ala Thr Lys Tyr Asn Glu Lys Phe
        50                  55                  60

Lys Gly Lys Ala Lys Leu Thr Ser Asp Lys Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Asn Tyr Tyr Gly Ser Lys Phe Ala Met Asp Tyr Trp Gly Gln Gly
                100                 105                 110

Thr Ser Val Thr Val Ser Ser
            115
```

-continued

```
<210> SEQ ID NO 18
<211> LENGTH: 107
<212> TYPE: PRT
<213> ORGANISM: artificial sequence
<220> FEATURE:
<223> OTHER INFORMATION: Synthetic

<400> SEQUENCE: 18

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Ser Trp Tyr Gln Arg Lys Pro Asp Gly Ala Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Ala Asp Tyr Ser Leu Thr Ile Ser Asn Leu Glu Gln
65                  70                  75                  80

Glu Asp Ile Ala Thr Tyr Phe Cys Gln Gln Gly Ile Thr Leu Pro Phe
                85                  90                  95

Thr Phe Gly Gly Gly Thr Lys Leu Glu Ile Lys
            100                 105

<210> SEQ ID NO 19
<211> LENGTH: 119
<212> TYPE: PRT
<213> ORGANISM: artificial sequence
<220> FEATURE:
<223> OTHER INFORMATION: Synthetic

<400> SEQUENCE: 19

Glu Val Gln Leu Val Glu Ser Gly Gly Gly Leu Val Gln Pro Lys Gly
1               5                   10                  15

Ser Leu Ser Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
        50                  55                  60

Ser Val Lys Asp Arg Phe Thr Ile Ser Arg Asp Asp Ser Gln Ser Met
65                  70                  75                  80

Leu Tyr Leu Gln Met Thr Asn Leu Lys Thr Glu Asp Thr Ala Met Tyr
                85                  90                  95

His Cys Val Arg Ser Leu Gly Arg Ala Phe Val Tyr Trp Gly Gln Gly
            100                 105                 110

Thr Leu Val Thr Val Ser Ser
        115

<210> SEQ ID NO 20
<211> LENGTH: 115
<212> TYPE: PRT
<213> ORGANISM: artificial sequence
<220> FEATURE:
<223> OTHER INFORMATION: Synthetic

<400> SEQUENCE: 20

Gln Leu Val Leu Thr Gln Ser Ser Ser Ala Ser Phe Ser Leu Gly Ala
1               5                   10                  15

Ser Ala Lys Leu Thr Cys Thr Leu Ser Ser Gln His Ser Thr Tyr Ile
                20                  25                  30
```

-continued

```
Ile Glu Trp Tyr Gln Gln Pro Leu Lys Pro Pro Lys Tyr Val Met
         35                  40                  45
Glu Leu Lys Lys Asp Gly Ser His Ser Thr Gly Glu Gly Ile Pro Asp
 50                  55                  60
Arg Phe Ser Gly Ser Ser Gly Ala Asp Arg Tyr Leu Ser Ile Ser
 65                  70                  75                  80
Asn Ile Gln Pro Glu Asp Glu Ala Ile Tyr Ile Cys Gly Val Gly Asn
                 85                  90                  95
Thr Ile Lys Glu Gln Phe Val Tyr Val Phe Gly Gly Gly Thr Lys Val
            100                 105                 110
Thr Val Leu
        115

<210> SEQ ID NO 21
<211> LENGTH: 449
<212> TYPE: PRT
<213> ORGANISM: artificial sequence
<220> FEATURE:
<223> OTHER INFORMATION: Synthetic

<400> SEQUENCE: 21

Glu Val Gln Leu Gln Gln Ser Gly Pro Glu Leu Val Lys Pro Gly Ala
 1               5                  10                  15
Ser Val Lys Met Ser Cys Lys Ala Ser Gly Tyr Thr Phe Thr Ser Tyr
             20                  25                  30
Val Met His Trp Leu Lys Gln Lys Pro Gly Gln Gly Leu Glu Trp Ile
         35                  40                  45
Gly Tyr Ile Asn Pro Tyr Asn Asp Gly Thr Lys Tyr Asn Glu Lys Phe
 50                  55                  60
Lys Gly Lys Ala Lys Leu Thr Ser Asp Lys Ser Ser Ser Thr Ala Tyr
 65                  70                  75                  80
Met Glu Leu Ser Ser Leu Thr Ser Glu Asp Ser Ala Val Tyr Tyr Cys
                 85                  90                  95
Ala Asn Tyr Tyr Gly Ser Lys Phe Ala Met Asp Tyr Trp Gly Gln Gly
            100                 105                 110
Thr Ser Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
```

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 22
<211> LENGTH: 449
<212> TYPE: PRT
<213> ORGANISM: artificial sequence
<220> FEATURE:
<223> OTHER INFORMATION: Synthetic

<400> SEQUENCE: 22

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Leu Lys Gln Lys Pro Gly Gln Gly Leu Glu Trp Ile
        35                  40                  45

Gly Tyr Ile Asn Pro Tyr Asn Asp Ala Thr Lys Tyr Asn Glu Lys Phe
    50                  55                  60

Lys Gly Lys Ala Lys Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Asn Tyr Tyr Gly Ser Lys Phe Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

-continued

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 23
<211> LENGTH: 445
<212> TYPE: PRT
<213> ORGANISM: artificial sequence
<220> FEATURE:
<223> OTHER INFORMATION: Synthetic

<400> SEQUENCE: 23

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Leu Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Lys Leu Thr Ser Asp Lys Ser Ser Ser Thr Ala Tyr
65                  70                  75                  80

```
Met Glu Leu Ser Ser Leu Thr Ser Glu Asp Ser Ala Val Tyr Tyr Cys
                 85                  90                  95

Ala Asn Tyr Tyr Gly Ser Lys Phe Ala Met Asp Tyr Trp Gly Gln Gly
            100                 105                 110

Thr Ser Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 24
<211> LENGTH: 214
<212> TYPE: PRT
<213> ORGANISM: artificial sequence
<220> FEATURE:
<223> OTHER INFORMATION: Synthetic
```

<400> SEQUENCE: 24

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Ser Trp Tyr Gln Arg Lys Pro Asp Gly Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Ala Asp Tyr Ser Leu Thr Ile Ser Asn Leu Glu Gln
65                  70                  75                  80

Glu Asp Ile Ala Thr Tyr Phe Cys Gln Gln Gly Ile Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 214
<212> TYPE: PRT
<213> ORGANISM: artificial sequence
<220> FEATURE:
<223> OTHER INFORMATION: Synthetic

<400> SEQUENCE: 25

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Ser Trp Tyr Gln Arg Lys Pro Asp Gly Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Ala Asp Tyr Ser Leu Thr Ile Ser Asn Leu Glu Gln
65                  70                  75                  80

Glu Asp Ile Ala Thr Tyr Phe Cys Gln Gln Gly Ile Thr Leu Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 26
<211> LENGTH: 449
<212> TYPE: PRT
<213> ORGANISM: artificial sequence
<220> FEATURE:
<223> OTHER INFORMATION: Synthetic

<400> SEQUENCE: 26

```
Glu Val Gln Leu Val Glu Ser Gly Gly Gly Leu Val Gln Pro Lys Gly
1               5                   10                  15

Ser Leu Ser Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Thr Asn Leu Lys Thr Glu Asp Thr Ala Met Tyr
                85                  90                  95

His Cys Val Arg Ser Leu Gly Arg Ala Phe Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 27
<211> LENGTH: 221
<212> TYPE: PRT
<213> ORGANISM: artificial sequence
<220> FEATURE:
<223> OTHER INFORMATION: Synthetic

<400> SEQUENCE: 27

Gln Leu Val Leu Thr Gln Ser Ser Ser Ala Ser Phe Ser Leu Gly Ala
1               5                   10                  15

Ser Ala Lys Leu Thr Cys Thr Leu Ser Ser Gln His Ser Thr Tyr Ile
            20                  25                  30

Ile Glu Trp Tyr Gln Gln Pro Leu Lys Pro Pro Lys Tyr Val Met
        35                  40                  45

Glu Leu Lys Lys Asp Gly Ser His Ser Thr Gly Glu Gly Ile Pro Asp
    50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asn
                85                  90                  95

Thr Ile Lys Glu Gln Phe Val Tyr Val Phe Gly Gly Gly Thr Lys Val
            100                 105                 110

Thr Val Leu Gly Gln Pro Lys Ala Asn Pro Thr Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Gly Ser Pro Val Lys Ala Gly Val Glu Thr Thr Lys Pro Ser Lys Gln
                165                 170                 175
```

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220

<210> SEQ ID NO 28
<211> LENGTH: 445
<212> TYPE: PRT
<213> ORGANISM: artificial sequence
<220> FEATURE:
<223> OTHER INFORMATION: Synthetic

<400> SEQUENCE: 28

Glu Val Gln Leu Val Glu Ser Gly Gly Gly Leu Val Gln Pro Lys Gly
1               5                   10                  15

Ser Leu Ser Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Thr Asn Leu Lys Thr Glu Asp Thr Ala Met Tyr
                85                  90                  95

His Cys Val Arg Ser Leu Gly Arg Ala Phe Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

```
Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 29
<211> LENGTH: 119
<212> TYPE: PRT
<213> ORGANISM: artificial sequence
<220> FEATURE:
<223> OTHER INFORMATION: Synthetic

<400> SEQUENCE: 29

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Thr Phe Thr Ser Tyr
            20                  25                  30

Val Met His Trp Leu Arg Gln Met Pro Gly Lys Gly Leu Glu Trp Met
        35                  40                  45

Gly Tyr Ile Asn Pro Tyr Asn Asp Gly Thr Lys Tyr Asn Glu Lys Phe
    50                  55                  60

Lys Gly Gln Val Thr Ile Ser Ser Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Asn Tyr Tyr Gly Ser Lys Phe Ala Met Asp Tyr Trp Gly Gln Gly
            100                 105                 110

Thr Met Val Thr Val Ser Ser
        115

<210> SEQ ID NO 30
<211> LENGTH: 107
<212> TYPE: PRT
<213> ORGANISM: artificial sequence
<220> FEATURE:
<223> OTHER INFORMATION: Synthetic

<400> SEQUENCE: 30

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
    50                  55                  60
```

```
Ser Gly Ser Gly Thr Asp Tyr Thr Leu Thr Ile Ser Ser Leu Gln Pro
 65                  70                  75                  80

Glu Asp Phe Ala Thr Tyr Phe Cys Gln Gln Gly Ile Thr Leu Pro Trp
                 85                  90                  95

Thr Phe Gly Gln Gly Thr Lys Val Glu Ile Lys
                100                 105

<210> SEQ ID NO 31
<211> LENGTH: 449
<212> TYPE: PRT
<213> ORGANISM: artificial sequence
<220> FEATURE:
<223> OTHER INFORMATION: Synthetic

<400> SEQUENCE: 31

Glu Val Gln Leu Val Gln Ser Gly Ala Glu Val Lys Lys Pro Gly Glu
 1               5                  10                  15

Ser Leu Lys Ile Ser Cys Lys Ala Ser Gly Tyr Thr Phe Thr Ser Tyr
                 20                  25                  30

Val Met His Trp Leu Arg Gln Met Pro Gly Lys Gly Leu Glu Trp Met
             35                  40                  45

Gly Tyr Ile Asn Pro Tyr Asn Asp Gly Thr Lys Tyr Asn Glu Lys Phe
 50                  55                  60

Lys Gly Gln Val Thr Ile Ser Ser Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Asn Tyr Tyr Gly Ser Lys Phe Ala Met Asp Tyr Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 32
<211> LENGTH: 214
<212> TYPE: PRT
<213> ORGANISM: artificial sequence
<220> FEATURE:
<223> OTHER INFORMATION: Synthetic

<400> SEQUENCE: 32

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ile Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 33
<211> LENGTH: 445
<212> TYPE: PRT
<213> ORGANISM: artificial sequence
<220> FEATURE:
<223> OTHER INFORMATION: Synthetic

<400> SEQUENCE: 33

| Glu | Val | Gln | Leu | Val | Gln | Ser | Gly | Ala | Glu | Val | Lys | Lys | Pro | Gly | Glu |
|---|---|---|---|---|---|---|---|---|---|---|---|---|---|---|---|
| 1 | | | | 5 | | | | | 10 | | | | | 15 | |

| Ser | Leu | Lys | Ile | Ser | Cys | Lys | Ala | Ser | Gly | Tyr | Thr | Phe | Thr | Ser | Tyr |
|---|---|---|---|---|---|---|---|---|---|---|---|---|---|---|---|
| | | | 20 | | | | | 25 | | | | | 30 | | |

| Val | Met | His | Trp | Leu | Arg | Gln | Met | Pro | Gly | Lys | Gly | Leu | Glu | Trp | Met |
|---|---|---|---|---|---|---|---|---|---|---|---|---|---|---|---|
| | | 35 | | | | | 40 | | | | | 45 | | | |

| Gly | Tyr | Ile | Asn | Pro | Tyr | Asn | Asp | Gly | Thr | Lys | Tyr | Asn | Glu | Lys | Phe |
|---|---|---|---|---|---|---|---|---|---|---|---|---|---|---|---|
| | 50 | | | | | 55 | | | | | 60 | | | | |

| Lys | Gly | Gln | Val | Thr | Ile | Ser | Ser | Asp | Lys | Ser | Ile | Ser | Thr | Ala | Tyr |
|---|---|---|---|---|---|---|---|---|---|---|---|---|---|---|---|
| 65 | | | | | 70 | | | | | 75 | | | | | 80 |

| Leu | Gln | Trp | Ser | Ser | Leu | Lys | Ala | Ser | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Ala | Asn | Tyr | Tyr | Gly | Ser | Lys | Phe | Ala | Met | Asp | Tyr | Trp | Gly | Gln | Gly |
|---|---|---|---|---|---|---|---|---|---|---|---|---|---|---|---|
| | | | 100 | | | | | 105 | | | | | 110 | | |

| Thr | Met | Val | Thr | Val | Ser | Ser | Ala | Ser | Thr | Lys | Gly | Pro | Ser | Val | Phe |
|---|---|---|---|---|---|---|---|---|---|---|---|---|---|---|---|
| | | 115 | | | | | 120 | | | | | 125 | | | |

| Pro | Leu | Ala | Pro | Cys | Ser | Arg | Ser | Thr | Ser | Glu | Ser | Thr | Ala | Ala | Leu |
|---|---|---|---|---|---|---|---|---|---|---|---|---|---|---|---|
| | 130 | | | | | 135 | | | | | 140 | | | | |

| Gly | Cys | Leu | Val | Lys | Asp | Tyr | Phe | Pro | Glu | Pro | Val | Thr | Val | Ser | Trp |
|---|---|---|---|---|---|---|---|---|---|---|---|---|---|---|---|
| 145 | | | | | 150 | | | | | 155 | | | | | 160 |

| Asn | Ser | Gly | Ala | Leu | Thr | Ser | Gly | Val | His | Thr | Phe | Pro | Ala | Val | Leu |
|---|---|---|---|---|---|---|---|---|---|---|---|---|---|---|---|
| | | | | 165 | | | | | 170 | | | | | 175 | |

| Gln | Ser | Ser | Gly | Leu | Tyr | Ser | Leu | Ser | Ser | Val | Val | Thr | Val | Pro | Ser |
|---|---|---|---|---|---|---|---|---|---|---|---|---|---|---|---|
| | | | 180 | | | | | 185 | | | | | 190 | | |

| Ser | Asn | Phe | Gly | Thr | Gln | Thr | Tyr | Thr | Cys | Asn | Val | Asp | His | Lys | Pro |
|---|---|---|---|---|---|---|---|---|---|---|---|---|---|---|---|
| | | 195 | | | | | 200 | | | | | 205 | | | |

| Ser | Asn | Thr | Lys | Val | Asp | Lys | Thr | Val | Glu | Arg | Lys | Cys | Cys | Val | Glu |
|---|---|---|---|---|---|---|---|---|---|---|---|---|---|---|---|
| | 210 | | | | | 215 | | | | | 220 | | | | |

| Cys | Pro | Pro | Cys | Pro | Ala | Pro | Pro | Val | Ala | Gly | Pro | Ser | Val | Phe | Leu |
|---|---|---|---|---|---|---|---|---|---|---|---|---|---|---|---|
| 225 | | | | | 230 | | | | | 235 | | | | | 240 |

| Phe | Pro | Pro | Lys | Pro | Lys | Asp | Thr | Leu | Met | Ile | Ser | Arg | Thr | Pro | Glu |
|---|---|---|---|---|---|---|---|---|---|---|---|---|---|---|---|
| | | | | 245 | | | | | 250 | | | | | 255 | |

| Val | Thr | Cys | Val | Val | Val | Asp | Val | Ser | His | Glu | Asp | Pro | Glu | Val | Gln |
|---|---|---|---|---|---|---|---|---|---|---|---|---|---|---|---|
| | | | 260 | | | | | 265 | | | | | 270 | | |

| Phe | Asn | Trp | Tyr | Val | Asp | Gly | Val | Glu | Val | His | Asn | Ala | Lys | Thr | Lys |
|---|---|---|---|---|---|---|---|---|---|---|---|---|---|---|---|
| | | 275 | | | | | 280 | | | | | 285 | | | |

| Pro | Arg | Glu | Glu | Gln | Phe | Asn | Ser | Thr | Phe | Arg | Val | Val | Ser | Val | Leu |
|---|---|---|---|---|---|---|---|---|---|---|---|---|---|---|---|
| | 290 | | | | | 295 | | | | | 300 | | | | |

| Thr | Val | Val | His | Gln | Asp | Trp | Leu | Asn | Gly | Lys | Glu | Tyr | Lys | Cys | Lys |
|---|---|---|---|---|---|---|---|---|---|---|---|---|---|---|---|
| 305 | | | | | 310 | | | | | 315 | | | | | 320 |

| Val | Ser | Asn | Lys | Gly | Leu | Pro | Ala | Pro | Ile | Glu | Lys | Thr | Ile | Ser | Lys |
|---|---|---|---|---|---|---|---|---|---|---|---|---|---|---|---|
| | | | | 325 | | | | | 330 | | | | | 335 | |

| Thr | Lys | Gly | Gln | Pro | Arg | Glu | Pro | Gln | Val | Tyr | Thr | Leu | Pro | Pro | Ser |
|---|---|---|---|---|---|---|---|---|---|---|---|---|---|---|---|
| | | | 340 | | | | | 345 | | | | | 350 | | |

| Arg | Glu | Glu | Met | Thr | Lys | Asn | Gln | Val | Ser | Leu | Thr | Cys | Leu | Val | Lys |
|---|---|---|---|---|---|---|---|---|---|---|---|---|---|---|---|
| | | 355 | | | | | 360 | | | | | 365 | | | |

| | | | | | | | | | | | | |
|---|---|---|---|---|---|---|---|---|---|---|---|---|
| Gly | Phe | Tyr | Pro | Ser | Asp | Ile | Ala | Val | Glu | Trp | Glu | Ser | Asn | Gly | Gln |
| 370 | | | | | 375 | | | | | 380 | | | | | |
| Pro | Glu | Asn | Asn | Tyr | Lys | Thr | Thr | Pro | Pro | Met | Leu | Asp | Ser | Asp | Gly |
| 385 | | | | | 390 | | | | | 395 | | | | | 400 |
| Ser | Phe | Phe | Leu | Tyr | Ser | Lys | Leu | Thr | Val | Asp | Lys | Ser | Arg | Trp | Gln |
| | | | | 405 | | | | | 410 | | | | | 415 | |
| Gln | Gly | Asn | Val | Phe | Ser | Cys | Ser | Val | Met | His | Glu | Ala | Leu | His | Asn |
| | | | 420 | | | | | 425 | | | | | 430 | | |
| His | Tyr | Thr | Gln | Lys | Ser | Leu | Ser | Leu | Ser | Pro | Gly | Lys |
| | | 435 | | | | | 440 | | | | | 445 |